(12) United States Patent
Ho

(10) Patent No.: US 9,879,316 B2
(45) Date of Patent: Jan. 30, 2018

(54) METHOD FOR COMPETITIVE ALLELE-SPECIFIC CDNA SYNTHESIS AND DIFFERENTIAL AMPLIFICATION OF THE CDNA PRODUCTS

(71) Applicant: Tho Huu Ho, Helsinki (FI)

(72) Inventor: Tho Huu Ho, Helsinki (FI)

( * ) Notice: Subject to any disclaimer, the term of this patent is extended or adjusted under 35 U.S.C. 154(b) by 63 days.

(21) Appl. No.: 14/397,405

(22) PCT Filed: Apr. 25, 2013

(86) PCT No.: PCT/FI2013/050470
§ 371 (c)(1),
(2) Date: Oct. 27, 2014

(87) PCT Pub. No.: WO2013/160563
PCT Pub. Date: Oct. 31, 2013

(65) Prior Publication Data
US 2015/0275286 A1    Oct. 1, 2015

(30) Foreign Application Priority Data

Apr. 25, 2012  (FI) .................................... 20125454

(51) Int. Cl.
*C12Q 1/68* (2006.01)
(52) U.S. Cl.
CPC ................................ *C12Q 1/6858* (2013.01)
(58) Field of Classification Search
CPC ............ C12Q 1/6858; C12Q 2521/107; C12Q 2525/155; C12Q 2525/161; C12Q 2531/113; C12Q 2537/161
See application file for complete search history.

(56) References Cited

U.S. PATENT DOCUMENTS

| 5,578,458 | A | 11/1996 | Caskey et al. | |
|---|---|---|---|---|
| 6,818,739 | B2 | 11/2004 | Sheridan et al. | |
| 2002/0025532 | A1 * | 2/2002 | Huang | C12Q 1/6827 435/6.11 |
| 2004/0058373 | A1 | 3/2004 | Winkler et al. | |
| 2010/0041563 | A1 * | 2/2010 | Li | C12Q 1/6858 506/9 |

FOREIGN PATENT DOCUMENTS

| EP | 1 686 190 A1 | | 8/2006 |
|---|---|---|---|
| WO | WO 91/15601 A1 | | 10/1991 |
| WO | WO 97/42345 | * | 11/1997 |
| WO | WO 2007/035893 A2 | | 3/2007 |
| WO | WO 2007/139811 A1 | | 12/2007 |
| WO | WO 2008/147887 A1 | | 12/2008 |
| WO | WO 2010/111682 A2 | | 9/2010 |
| WO | WO 2013/074874 | * | 5/2013 |

OTHER PUBLICATIONS

Dunbar, S. A., "Applications of Luminex® xMAP™ technology for rapid high-throughput multiplexed nucleic acid detection," Clinica Chimica Acta (2006), vol. 363, pp. 71-82.
International Search Report dated Aug. 15, 2013, in PCT International Application No. PCT/FI2013/050470.
Renaud et al., "Diagnostic accuracy of an allele-specific reverse transcriptase-PCR assay targeting the H275Y oseltamivir resistant mutation in 2009 pandemic influenza A/H1N1 virus," Journal of Clinical Virology (2010), vol. 49, pp. 21-25.
Search Report dated Feb. 8, 2013, in Finnish Patent Application No. 20125454.

* cited by examiner

*Primary Examiner* — Teresa E Strzelecka
(74) *Attorney, Agent, or Firm* — Birch, Stewart, Kolasch & Birch, LLP

(57) ABSTRACT

The present invention provides a method for the detection of the presence of RNA variants comprising the step of performing a competitive cDNA synthesis comprising a first primer specific to a first RNA variant, a second primer specific to a second RNA variant, an RNA-dependent DNA polymerase, and RNA from said sample as a template, wherein said first primer and said second primer comprise an allele-specific nucleotide portion, a target-specific sequence and tag units with a common sequence and/or a discriminating sequence so that the sequence of said tag units is not complementary to said first or second RNA variant, wherein each of the cDNA products obtained from said competitive cDNA synthesis consists of the sequence of only one primer extended by the sequence complementary to one of the target RNA variants.

22 Claims, 13 Drawing Sheets

A. Reverse transcription without wildtype-specific oligo nucleotide:

B. Reverse transcription with wildtype-specific primer:

C. Reverse transcription with non-extendable wildtype-specific oligonucleotide (3'-PO4):

D. Reverse transcription with non-extendable wildtype-specific oligonucleotide (3'-hexaA tail):

| Mutation-specific primers | Ct values | | ΔCt | Mis-priming / Correct priming |
|---|---|---|---|---|
| | Mutant RNA ($10^7$ copies) | Wildtype RNA ($10^7$ copies) | | |
| KRAS-12/Asp | 23.1 | 33.5 | 10.4 | 0.07 % |
| KRAS-12/Ala | 21.5 | 34 | 12.5 | 0.017 % |
| KRAS-12/Val | 20 | 32.6 | 12.6 | 0.016 % |
| KRAS-12/Ser | 25.2 | 35.7 | 10.5 | 0.07 % |
| KRAS-12/Arg | 21 | 34 | 13 | 0.012 % |
| KRAS-12/Cys | 24 | 35.5 | 11.5 | 0.035 % |

Figure 3.

Different ratio of the 1st form over the 2nd form of wildtype-specific primer

METHOD FOR COMPETITIVE ALLELE-SPECIFIC CDNA SYNTHESIS AND DIFFERENTIAL AMPLIFICATION OF THE CDNA PRODUCTS

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-05-26 0933-0656PUS1_ST25.txt" created on May 26, 2015 and is 10,831 bytes in size. The sequence listing contained in this .txt file is part of the specification and is hereby incorporated by reference herein in its entirety.

The present invention relates to methods and kits for use in detection and distinguishing different RNA variants of a target sequence. More specifically, in some embodiments, the present invention provides methods and kits for absolute or relative quantification of different RNA variants in a sample, comprising a rare RNA variant and an abundant RNA variant, with high sensitivity, specificity and selectivity. In particular, in some embodiments, the invention relates to an extraordinarily simple and highly selective method for RNA mutation detection and quantification referred to as allele-specific reverse transcription and polymerase chain reaction ("ART-PCR").

DESCRIPTION OF THE RELATED ART

Single nucleotide polymorphisms (SNPs) and point mutations are the most common type of genetic polymorphism (Altshuler, D. et al. Nature 2005, 437, 1299-1320). They have been widely investigated as important biomarkers in many research and clinical applications, particularly in diagnosis and management of genetic disorders including cancers (Lievre, A. et al. Cancer Res 2006, 66, 3992-3995) and infectious diseases (Garcia-Gonzalez, C. et al. Diagn Microbiol Infect Dis 2012, 72, 90-96; Tong, S. Y. et al. PLoS ONE 2011, 6, e21446)

Although various DNA mutation detection assays can identify the presence of specific mutations, the expression level of the mutant alleles of coding genes may vary and affect the phenotype of cells or tissues harboring these mutations. As a consequence, a quantitative assay for detection of RNA transcripts of mutant genes could more accurately reflect the effect brought upon the cells or tissues by the presence of a specific mutation. In addition, detection of RNA variants has also been valuable for identifying drug-resistance mutations within genomes of various RNA viruses, such as human immunodeficiency virus (HIV) and influenza viruses.

Various strategies for SNP genotyping or mutation detection have been well established by employing one or more properties of following processes: hybridization, primer extension or ligation (Chen, X., and Sullivan, P F, The Pharmacogeonomics Journal 2003, 3, 77-96) that utilized DNA samples as templates. To detect RNA variants, RNA samples first need to be reverse transcribed into cDNAs in a nonspecific manner; those cDNA products are later subjected to a method of DNA mutation detection (Singer-Sam, J., LeBon, J. M., Dai, A. & Riggs, A. D. PCR Methods Appl 1, 1992, 160-163; Stenman, J. et al. Nat Biotechnol 17, 1999, 720-722; Main, B. J. et al. BMC Genomics 10, 2009, 422). Currently, there is no optimal method for achieving allele specificity during cDNA synthesis, possibly due to the fact that reverse transcriptases can extend over a base mispair at the termini of a primer more efficiently than DNA-dependent DNA polymerases (Mendelman, L. V, Petruska, J and Goodman, M. F, J Biol Chem 1990, 265, 2338-2346)

SUMMARY OF THE INVENTION

An object of the present invention is a method for distinguishing between different RNA sequences.

An additional object of the present invention is a method to detect genetic polymorphism in known RNA sequences.

An additional object of the present invention is a method to detect a rare RNA variant in the excessive amount of the abundant RNA variant with high selectivity.

An additional object of the present invention is a method to quantitate the level of allele-specific gene expression An additional object of the present invention is a method to selectively amplify an RNA variant in a sample containing different RNA variants.

In some embodiments, the present inventions relates generally to methods, compositions and kits for use in discriminating sequence variation between different RNA variants. More specifically, in some embodiments, the present invention provides for methods, kits and compositions for quantitating rare (e.g. mutant) RNA variants, such as SNP or nucleotide insertions or deletions, in samples comprising abundant (e.g. wild type) RNA variants with high specificity. In particular, in some embodiments, the invention relates to a highly selective method for mutation detection using RNA samples referred to as Allele-specific Reverse Transcription and Polymerase Chain Reaction (ART-PCR).

In one aspect, the present invention provides a method for simultaneously detecting and/or quantitating multiple RNA variants or distinguishing between different RNA variants comprising the steps of:

a) performing a competitive cDNA synthesis comprising a first primer specific to a first RNA variant, a second primer specific to a second RNA variant, an RNA-dependent DNA polymerase, and RNA from said sample as a template, wherein said first primer and said second primer comprise an allele-specific nucleotide portion, a target-specific sequence and tag units with a common sequence and/or a discriminating sequence so that the sequence of said tag units is not complementary to said first or second RNA variant, wherein each of the cDNA products obtained from said competitive cDNA synthesis consists of the sequence of only one primer extended by the sequence complementary to one of the target RNA variants;

b) performing a polymerase chain reaction comprising a sense primer, an anti-sense primer and the competitive primer extension products obtained from step a) as templates, wherein said sense primer comprises a 3' sequence that is complementary to the sequence present in the extended part of both competitive cDNA products derived from the first and second RNA variant, and said anti-sense primer comprises a 3' sequence that is complementary to the complement of the common sequence of said tag units, so that the competitive cDNA synthesis products derived from the first RNA variant and the second RNA variant are amplified;

c) detecting the presence of amplification reaction products corresponding to the first and/or second RNA variant obtained from step b) utilizing the presence of the allele-specific nucleotide portion or the discriminating sequence of said tag units in said amplification reaction products.

In this embodiment, a subtle difference between the first variant and the second variant (e.g., a nucleotide substitution) is transformed in to a more significant difference between their corresponding cDNA products formed in step a) as a result of the discriminating sequences within tag units of the first primer and the second primer. At least part of these discriminating sequences within cDNA products will be amplified in step b) and incorporated in the amplification product, thus forming the basis for the detection, quantitation and distinguish between different variants.

In some embodiments of the method, which facilitate detection of a rare variant by enriching the amplification product of the second variant (e.g., rare variant) in comparison to that of the first variant (e.g., abundant variant), a third primer specific to the first RNA variant is also included in the cDNA synthesis reaction mixture of step a) in addition to the first primer and the second primer, wherein said third primer comprises the same or similar allele-specific nucleotide portion and target-specific sequence as the first primer but does not comprise tag units with the common sequence as in the first and second primer. The third primer competes with the first primer to initiate cDNA synthesis on the first RNA variant template (e.g., abundant variant) in a manner depending on relative molar concentrations of those primers. However, the cDNA product initiated by the third primer annealed to the first RNA variant will not be amplified in the step b) due to lacking priming site (common sequence) of the anti-sense primer in the step b). Consequently, amplification product of the second-primer-derived cDNA, which corresponds to the second RNA variant (e.g., rare variant), will be enriched in comparison to amplification product corresponding to the first RNA variant.

In some embodiment of the method, the third primer comprises tag units, which does not comprise the common sequence as in the first primer and the second primer. In other embodiment, the third primer does not comprise any tag units.

In another aspect, the present invention provides method for detecting and/or quantitating one RNA variant in a sample containing different RNA variants. In this method, all RNA variants serve as template for cDNA synthesis, however, only cDNA product resulted from the RNA variant under investigation is amplified and the cDNA product resulted from other RNA variants are not amplified. This selective amplification process can be achieved by designing different tag units for each allele-specific primer used in the cDNA synthesis reaction. Some of these methods can involve the following steps:
a) performing a competitive cDNA synthesis comprising a first primer specific to a first RNA variant, a second primer specific to a second RNA variant, an RNA dependent DNA polymerase, and RNA from said sample as a template, wherein said first primer and said second primer comprise an allele-specific nucleotide portion, a target-specific sequence and tag units with a discriminating sequence so that the sequence of said tag units is not complementary to said first or second RNA variant, wherein each of the extension products obtained from said competitive cDNA synthesis consists of the sequence of only one primer extended by the sequence complementary to one of the target RNA variants;
b) performing a polymerase chain reaction comprising a sense primer, an anti-sense primer and the competitive primer extension products obtained from step a) as templates, wherein said sense primer comprises a 3' sequence that is complementary to the sequence present in the extended part of both competitive cDNA products derived from the first and second RNA variant, and said anti-sense primer comprises a 3' sequence that is complementary to said discriminating sequence in the second primer, so that the competitive cDNA synthesis products derived from the second RNA variant are amplified and the competitive cDNA synthesis products derived from the first variant are not amplified;
c) detecting the presence of polymerase chain reaction products obtained from step b), wherein the presence of said polymerase chain reaction products confirms that said second RNA variant is present in said sample.

In some embodiment of the method, the first primer does not comprise tag units and the second primer comprises tag units. In some other embodiments, both the first primer and the second primer comprise tag units that are not identical.

In some embodiment of the method, the cDNA synthesis in step a) and the polymerase chain reaction in step b) are performed in a single vessel.

In another aspect, the present invention provides method for selective amplification of an RNA variant in a sample containing different RNA variants. Such amplification product may be used for further analysis of the RNA variant under investigation, for example, genotyping of other SNP positions of that RNA variant. Some of these methods can involve the following steps:
a) performing a competitive cDNA synthesis comprising a first primer specific to a first RNA variant, a second primer specific to a second RNA variant, a RNA dependent DNA polymerase, and RNA from said sample as a template, wherein said first primer and said second primer comprise an allele-specific nucleotide portion, a target-specific sequence and tag units with a discriminating sequence so that the sequence of said tag units is not complementary to said first or second RNA variant, wherein each of the extension products obtained from said competitive cDNA synthesis consists of the sequence of only one primer extended by the sequence complementary to one of the target RNA variants;
b) performing a polymerase chain reaction comprising a sense primer, an anti-sense primer and the competitive primer extension products obtained from step a) as templates, wherein said sense primer comprises a 3' sequence that is complementary to the sequence present in the extended part of both competitive cDNA products derived from the first and second RNA variant, and said anti-sense primer comprises a 3' sequence that is complementary to said discriminating sequence in the second primer, so that the competitive cDNA synthesis products derived from the second RNA variant are amplified and the competitive cDNA synthesis products derived from the first variant are not amplified;

In another aspect, the present invention provides kit for the detection of the presence of RNA variants in a sample comprising RNA, the kit comprising one or two primers specific to a first RNA variant, and one primer specific to a second RNA variant, wherein the primer specific to a second RNA variant and at least one of the primers specific to a first RNA variant comprise tag units with a common sequence and/or discriminating sequence so that the sequence of said tag units is not completely complementary to said first or second RNA variant, and wherein said kit do not comprise a primer pair for amplification of the first RNA variant or second RNA variant so that both primers of said primer pair are complementary to said first or second RNA variant.

In some embodiment of the kit, the reaction mixture further comprises a primer pair consisting of a sense primer and an anti-sense primer, wherein said sense primer comprises a 3' sequence that is complementary to the complement of the sequence present in both the first and second RNA variant, and said anti-sense primer comprises a 3' sequence that is complementary to the complement of the common sequence of said tag units.

In some embodiment of the kit, the reaction mixture further comprise a detector probe comprising the discriminating sequence of one of the primers or a sequence complementary to said discriminating sequence.

In some embodiment of the kit, the tag units form a 5' nucleotide tail.

In some embodiment of the kit, the reaction mixture further comprises an RNA-dependent polymerase.

In another aspect, the present invention provides kit for the detection of the presence of an RNA variant in a sample comprising RNA, the kit comprising one primer specific to a first RNA variant, and one primer specific to a second RNA variant, wherein the two primers comprise an allele-specific nucleotide portion, a target-specific sequence and tag units with a discriminating sequence so that the sequence of said tag units is not completely complementary to said first or second RNA variant, and wherein said kit do not comprise a primer pair for amplification of the first RNA variant or second RNA variant so that both primers of said primer pair are complementary to said first or second RNA variant.

In some embodiment of the kit, the reaction mixture further comprise a primer pair consisting of a sense primer and an anti-sense primer, wherein said sense primer comprises a 3' sequence that is complementary to the complement of the sequence present in both the first and second RNA variant, and said anti-sense primer comprises a 3' sequence that is complementary to the complement of said discriminating sequence in one of the two primers.

In some embodiment of the kit, the reaction mixture further comprise a detector probe comprising the discriminating sequence of one of the primers or a sequence complementary to said discriminating sequence.

In another aspect, the present invention provides composition for use in the detection of the presence of RNA variants in a sample comprising RNA, the composition comprises up to two primers specific to a first RNA variant and only one primer specific to a second RNA variant, wherein at least one of the primers specific to the first RNA variant and the primer specific to a second RNA variant comprise an allele-specific nucleotide portion, a target-specific sequence and tag units with a common sequence and/or a discriminating sequence so that the sequence of said tag units is not complementary to said first or second RNA variant.

In some embodiments of the composition, the composition can further comprise template RNA suspected to comprise one or more RNA variants of interest.

In some embodiments of the composition, the composition can further comprise an RNA-dependent polymerase.

In some embodiments of the composition, the composition can further comprise a primer pair consisting of a sense primer and an anti-sense primer, wherein said sense primer comprises a 3' sequence that is complementary to the complement of the sequence present in both the first and second RNA variant, and said anti-sense primer comprises a 3' sequence that is complementary to the complement of said discriminating sequence in one of the two primers.

In some embodiments of the composition, the tag units form a 5' nucleotide tail.

In another aspect, the present invention provides composition for use in the detection of the presence of RNA variants in a sample comprising RNA, the composition comprises only one primer specific to a first RNA variant and only one primer specific to a second RNA variant, wherein the two primers comprise an allele-specific nucleotide portion, a target-specific sequence and tag units with a discriminating sequence so that the sequence of said tag units is not completely complementary to said first or second RNA variant.

In some embodiments of the composition, the composition can further comprise template RNA suspected to comprise one or more RNA variants of interest.

In some embodiments of the composition, the composition can further comprise an RNA-dependent polymerase.

In some embodiments of the composition, the composition can further comprise a primer pair consisting of a sense primer and an anti-sense primer, wherein said sense primer comprises a 3' sequence that is complementary to the complement of the sequence present in both the first and second RNA variant, and said anti-sense primer comprises a 3' sequence that is complementary to the complement of said discriminating sequence in one of the two primers.

In some embodiments of the composition, the tag units form a 5' nucleotide tail.

Other and further objects features and advantages will be apparent from the following description of the presently preferred embodiments of the invention given for the purpose of disclosure when taken in conjunction with the accompanying drawings. It is to be understood that both the foregoing general description and following detail description are exemplary and explanatory only and are not restrictive of the invention, as claimed.

BRIEF DESCRIPTION OF THE DRAWINGS

FIG. 1 demonstrates the basic principle of the competitive allele-specific cDNA synthesis and differential amplification method.

FIG. 3 depicts the specificity of detection of KRAS mutant RNA transcripts using ART-PCR assays in exemplary embodiments.

DETAILED DESCRIPTION OF THE PRESENT INVENTIONS

Definitions

Figure 1A:
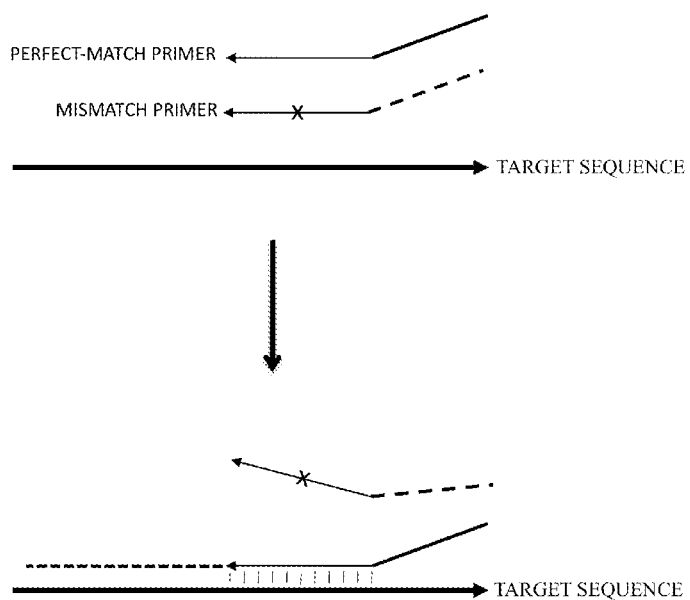
FIG. 1A: When two "competitive allele-specific primers" compete for a single sequence comprising one RNA variant of target sequence, a primer with perfectly matched "allele-specific nucleotide portion" will initiate cDNA synthesis in preference to a primer comprising mismatched allele-specific nucleotide portion. By determining which competitive allele-specific primer incorporated in competitive cDNA product, the identity of target sequence will be indicated.
Figure 1B:
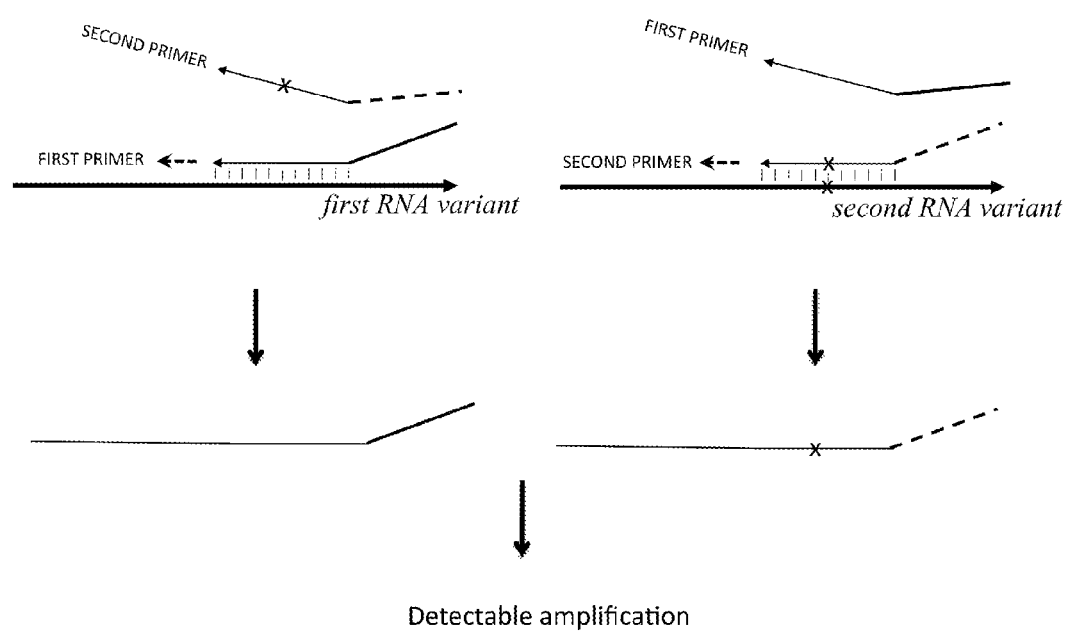
FIG. 1B: Discriminating sequences of different competitive allele-specific primers result in sufficient differences between competitive cDNA products. Such differences enable them to be conveniently identified and distinguished in a subsequent detectable amplification.

The term "nucleic acid" is intended to encompass a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, viral genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. Nucleic acids may include modified bases to alter the function or behavior of the nucleic acid, e.g., addition of a LNA to increase the melting temperature of the duplex of nucleic acid. As used herein, a "sequence" of a nucleic acid refers to the sequence of bases, which make up a nucleic acid. Throughout this application, nucleic acids are designated as having a 5'-terminus and a 3'-terminus.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "non-nucleotide unit" is a unit that does not significantly participate in hybridization of a polymer. Such units must not, for example, participate in any significant hydrogen bonding with a nucleotide, and would exclude units having as a component one of the five nucleotide bases or analogs thereof.

As used herein, the term "RNA variant" or "RNA allele" refers generally to alternative RNA sequences at the same physical locus on a RNA segment. A RNA variant can refer to RNA sequences which differ between the same physical locus within a single cell or organism or which differ at the same physical locus in multiple cells or organisms. In some instances, an RNA variant can correspond to a single nucleotide difference at a particular physical locus. In other embodiments an RNA variant can correspond to more significant difference, such as nucleotide (single or multiple) insertions or deletions.

As used herein, the term "rare RNA variant" refers to an RNA variant present at a lower level in a sample as compared to an alternative variant. For instance, the rare RNA variant may be found at a frequency less than $1/10$, $1/100$, $1/1,000$, $1/10,000$, $1/100,000$, $1/1,000,000$, $1/10,000,000$, $1/100,000,000$ or $1/1,000,000,000$ compared to another RNA variant for a target sequence. Alternatively, the rare variant can be, for example, less than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, or 1,000,000 copies per 1, 10, 100, 1,000 micro liters of a sample or a reaction volume.

As used herein, the terms "abundant RNA variant" may refer to an RNA variant present at a higher level in a sample as compared to an alternative variant. For instance, the abundant RNA variant may be found at a frequency greater than 10×, 100×, 1,000×, 10,000×, 100,000×, 1,000,000× 10,000,000×, 100,000,000× or 1,000,000,000× compared to another allelic variant for a given SNP or gene. Alternatively, the abundant allelic variant can be, for example, greater than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, 1,000,000 copies per 1, 10, 100, 1,000 micro liters of a sample or a reaction volume.

As used herein, a "target sequence" present in a nucleic acid sample is a strand of RNA to be primed and extended by a "competitive allele-specific primer". A target sequence may be either single-stranded or in a duplex with its complementary sequence. In certain embodiments, a target sequence may not be present in a nucleic acid sample, but may be present later as a result of transcription from another nucleic acid present in said nucleic acid sample. Target sequence as used herein includes at least two target RNA variants, a first RNA variant and a second RNA variant. Typically a target sequence includes cRNA, vRNA, rRNA, tRNA, or mRNA from viruses, bacteria, fungi, or eukaryotic cells. Target sequences may be from any number of sources based on the purpose of the assay being carried out. Sources of target sequences include, but are not limited to, clinical specimens (e.g., blood, either whole blood or platelets, urine, saliva, feces, semen, or spinal fluid); environmental samples (e.g., water or soil samples); food samples; beverages; industrial samples (e.g., products and process materials, including water); seed stocks; total cellular RNA; or product of a process, such as cDNA synthesis, amplification. Target sequence of the present invention may be purified to some degree prior to the amplification reactions described herein, but in other cases, the sample is added to the cDNA synthesis and amplification reaction without any further manipulations.

As used herein, the term "oligonucleotide" refers to any polymer of two or more of nucleotides, nucleosides, nucleobases or related compounds used as a reagent in the cDNA synthesis and amplification methods of the present invention. The oligonucleotide may be DNA and/or RNA and/or analogs thereof. The term oligonucleotide does not denote any particular function to the reagent; rather, it is used generically to cover all such reagents described herein. Specific oligonucleotides of the present invention are described in more detail below. As used herein, an oligonucleotide can be virtually any length, limited only by its specific function in the cDNA synthesis and amplification reaction. Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include, but are not limited to base modifications, sugar modifications or backbone modifications. While design and sequence of oligonucleotides for the present invention depend on their function as described below, several variables must generally be taken into account. Among the most critical are: length, G/C content, melting temperature (Tm), Gibb free energy (G), specificity, self-complementarity and complementarity with other oligonucleotides in the system, polypyrimidine (T, C) or polypurine (A, G) stretches, and the 3'-end sequence. Controlling for these and other variables is a standard and well-known aspect of oligonucleotide design, and various computer programs are readily available to screen large numbers of potential oligonucleotides for optimal ones.

An "allele-specific primer" or "primer specific to an RNA variant" as used herein refers to an oligonucleotide that hybridizes to sequence comprising respective RNA variant of target sequence and initiate cDNA synthesis when placed under conditions, which induce synthesis. Allele-specific primers are specific for a particular RNA variant of a given target sequence and can be designed to detect a difference of as little as one nucleotide in the target sequence. Allele-specific primer comprises a target-specific portion, an allele-specific portion and optionally a tag unit or tag units.

The term "competitive allele-specific primers" as used herein refers to, at least two allele-specific primers present in a single reaction of cDNA synthesis, the first allele-specific primers and the second allele-specific primer. Each allele-specific primer competes successfully for hybridizing and initiating cDNA synthesis from sequence comprising respective RNA variant of target sequence to form a competitive cDNA product. In addition, the differences between sequences of different competitive allele-specific primers are more significant than those between sequences of different RNA variants. As a result, the cDNA product derived from each competitive allele-specific primer will be more readily detected and/or discriminated using a detectable amplification method.

As used herein, the term "target-specific portion" or "target-specific sequence" refers to the region of an allele-specific primer that hybridizes to target sequence. In some embodiments, the target-specific portion of the allele-specific primer may comprise an allele-specific nucleotide portion. In other embodiment, the target-specific portion of the allele-specific primer is adjacent to the 3' allele-specific nucleotide portion.

As used herein, the terms "allele-specific nucleotide portion" or "allele-specific nucleotide" refers to a nucleotide or nucleotides in the allele-specific primer that can selectively hybridize and/or be extended from one RNA variant at a given locus to the exclusion of the other at the same locus. Accordingly, "an allele-specific nucleotide portion" is in its broader sense a RNA variant-specific nucleotide portion. In some embodiments, an allele-specific nucleotide portion is around the centre of the allele-specific primer to deliberately destabilize its duplex with the alternative RNA variant of target sequence. In some other embodiments, an allele-specific nucleotide portion is at the 3' end of the allele-specific primer to inhibit the incorporation of the next nucleotide when it hybridizes to an alternative RNA variant of the target sequence.

As used herein, the term "tag units" refers to one or more nucleotides or non-nucleotide units that are different from a nucleotide fully complementary with corresponding nucleotides on the target sequence when the allele-specific primer stably hybridizes to the sequence comprising the respective RNA variant of target sequence. In some embodiments, the tag units may be located 5' to the target-specific portion, i.e. the primer comprises a 5' nucleotide tail. In some other embodiments, the tag units may be located inside the target-specific portion. In some further embodiments, the tag units may be located at both said regions. The tag units may comprise "a common sequence" and "a discriminating sequence". The common sequence is a portion of identical nucleotide sequence in competitive allele-specific primers used in the same cDNA synthesis. The term "discriminating sequence" refers to the differential portions of nucleotide sequence in the competitive allele-specific primers having essentially different nucleotide sequences in order to facilitate the detection of cDNA products derived from each of the competitive allele-specific primers and enable amplification of said cDNA products using for example separate downstream PCR primers specific to said discriminating sequence in each primer.

The term "conventionally complementary" refers to two nucleotides on opposite strands forming normal bonding pairs, including A-T, A-U and G-C, when these opposite strands stably hybridize to each other. Thus, the conventional base pairing, A-T, A-U or G-C, is not seen in "mismatched bases". A variety of mismatched bases can occur, for example, but not limited to G-G, C-C, A-A, T-T, U-U, A-G, A-C, T-U, T-G, T-C, U-G or U-C.

A "competitive cDNA product" as used herein refers to the nucleic acid formed during cDNA synthesis with competitive allele-specific primers in the presence of sequence comprising either or both RNA variants of target sequence. Competitive cDNA products comprise the sequence of the respective competitive allele-specific primer at its 5' end, and the remaining sequence is complementary to the target sequence.

In the case of unhybridized competitive allele-specific primers, the term "inactivating" means that the competitive allele-specific primers is altered from an "active" conformation which permits them to hybridize to the target sequence and/or the complementary sequence of competitive cDNA products, to an "inactive" conformation which blocks or otherwise prevents them from hybridizing to the target sequence and/or the complementary sequence of competitive cDNA products. For example, these competitive allele-specific primers can initiate cDNA synthesis under quite low stringency conditions, but they will not function as primers under higher stringent conditions. Alternatively, the unhybridized competitive allele-specific primers may be altered by an enzyme, such as an exonuclease having a 3'-to-5' or 5'-to-3' activity for removing nucleotides from their sequences. Other inactivating means include chemicals for altering the competitive allele-specific primers so that it is incapable of hybridizing to a target nucleic acid sequence and/or the complementary sequence of competitive cDNA products under amplification conditions.

As used herein, the term "removing" refers to the physical separation of competitive cDNA products from unhybridized competitive allele-specific primers. Competitive cDNA products can be physically separated from unhybridized competitive allele-specific primers present in a nucleic acid sample by a variety of techniques known to those skilled in the art. By way of example, competitive cDNA products can be bound to a solid support and immobilized in a nucleic acid sample while unbound material is removed. To remove unbound material, the solid support can be subjected to one or more wash/rinse steps. The wash steps are intended to remove remaining unhybridized competitive allele-specific primers and potentially interfering cellular or sample material. A rinse step is typically included where the wash solution contains a component that is inhibitory to amplification when present at a sufficiently high concentration, such as a detergent. The solid support preferably binds specifically to target nucleic acids or competitive cDNA products to prevent unhybridized competitive allele-specific primers from entering into the amplification reaction. An example for capturing, immobilizing and purifying target nucleic acids is disclosed by Weisburg et al., "Two-Step Hybridization and Capture of a Polynucleotide," U.S. Pat. No. 6,534,273.

By "detectable amplification" is meant that a detectable signal associated with an amplification product in an amplification reaction mixture rises above a predetermined background or threshold level (end-point amplification) or rises above a background or threshold level within a predetermined period of time (real-time amplification). See, e.g., Light et al., "Method for Determining the Amount of an Analyte in a Sample," U.S. Pat. Appln. Pub. No. US 2006-0276972, paragraphs 506-549. The amplification product contains a sequence having sequence identity with a target nucleic acid sequence or its complement and can be detected with, for example, an intercalating dye or a detection probe having specificity for a region of the target nucleic acid sequence or its complement.

As used herein, the term "PCR amplifying" or "PCR amplification" refers generally to cycling polymerase-mediated exponential amplification of nucleic acids employing primers that hybridize to complementary strands, as described for example in Innis et al, PCR Protocols: A Guide to Methods and Applications, Academic Press (1990). Devices have been developed that can perform thermal cycling reactions with compositions containing fluorescent indicators which are able to emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; 6,174,670; and 6,814,934 and include, but are not limited to, the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), the ABI GeneAmp® 7500 Sequence Detection System (Applied Biosystems, Foster City, Calif.), the StepOne™ Real-Time PCR System (Applied Biosystems, Foster City, Calif.) and the ABI GeneAmp® 7900 Sequence Detection System (Applied Biosystems, Foster City, Calif.).

As used herein, the term "thermostable" or "thermostable polymerase" refers to an enzyme that is heat stable or heat resistant and catalyzes polymerization of deoxyribonucleotides to form cDNA products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90° C.-100° C. under conditions such as is typically required for PCR amplification.

As used herein, the term "detector probe" refers to any of a variety of signaling molecules indicative of amplification. For example, SYBR® Green and other DNA-binding dyes are detector probes. Some detector probes can be sequence-based, for example 5' nuclease probes. Various detector probes are known in the art, for example TaqMan® probes (See U.S. Pat. No. 5,538,848) various stem-loop molecular beacons (See, e.g., U.S. Pat. Nos. 6,103,476 and 5,925,517 and Tyagi and Kramer, Nature Biotechnology 1996, 14:303-308), stemless or linear beacons (See, e.g., WO 99/21881), PNA Molecular Beacons™ (See, e.g., U.S. Pat. Nos. 6,355,421 and 6,593,091), linear PNA beacons (See, e.g., Kubista et al., 2001, SPIE 4264:53-58), non-FRET probes (See, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhianga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al, 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can comprise reporter dyes such as, for example, 6-carboxyfluorescein (6-FAM) or tetrachlorofluorescin (TET). Detector probes can also comprise quencher moieties such as tetramethylrhodamine (TAMRA), Black Hole Quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher on the other, wherein hybridization of the two probes together on a target quenches the signal, or wherein hybridization on a target alters the signal signature via a change in fluorescence. Detector probes can also comprise sulfonate derivatives of fluorescein dyes with SO3 instead of the carboxylate group, phosphoramidite forms of fluorescein, phosphoramidite forms of CY5 (available, for example, from Amersham Biosciences-GE Healthcare).

As used herein, the term "common locus-specific primer" refers to an oligonucleotide sequence that hybridizes to all competitive cDNA products in a PCR reaction, and which can effectuate primer extension reaction from said products.

As used herein, the term "differential primer" refers to an oligonucleotide comprising a region of certain or all competitive cDNA products, which hybridizes to the complementary sequence of said competitive cDNA products and which functions in concert with common locus-specific primer in a PCR reaction to amplify said competitive cDNA products. Accordingly, in some embodiments, the common locus-specific primer serves as a sense PCR primer and the differential primer serve as an anti-sense PCR primer, or vice versa. In some embodiments, the differential primer effectuates selective amplification of only one competitive cDNA product. In some other embodiments, the differential primer effectuates the co-amplification of a group of competitive cDNA products, but creates desirable differences between amplicons as a result of differential portions in said group of competitive cDNA products between the priming sites of the common locus-specific primer and the differential primer.

Embodiments

The present invention is directed to a method for the detection of the presence of RNA variants in a sample containing RNA, which is suspected to comprise one or more RNA variants of interest, the method comprising the steps of:

a) performing a competitive cDNA synthesis comprising a first primer specific to a first RNA variant, a second primer specific to a second RNA variant, an RNA-dependent DNA polymerase, and RNA from said sample as a template, wherein said first primer and said second primer comprise an allele-specific nucleotide portion, a target-specific sequence and tag units with a common sequence and/or a discriminating sequence so that the sequence of said tag units is not complementary to said first or second RNA variant, wherein each of the cDNA products obtained from said competitive cDNA synthesis consists of the sequence of only one primer extended by the sequence complementary to one of the target RNA variants;
b) performing an amplification reaction so that at least part of the cDNA synthesis products obtained from step a) are amplified;
c) detecting the presence of amplification reaction products corresponding to the first and/or second RNA variant obtained from step b) utilizing the presence of the allele-specific nucleotide portion or the discriminating sequence of said tag units in said amplification reaction products.

In further embodiments, the present invention provides methods for detecting and/or quantitating one RNA variant in a sample containing different RNA variants. Some of these methods can involve the following steps:

a): (i) hybridizing a first allele-specific primer to a sequence comprising first RNA variant of target sequence; (ii) hybridizing a second allele-specific primer to a sequence comprising second RNA variant of target sequence; (iii) competitively extending of both first and second allele-specific primer from sequence comprising first and second RNA variants, respectively, to form competitive cDNA products; and then preferably reducing in said competitive cDNA synthesis the effective concentration of competitive allele-specific primers which have not formed part of said competitive cDNA products and which are in a form capable of producing a competitive cDNA product with said target sequence and/or the complementary sequence of said competitive cDNA products, wherein said first allele-specific primer and said second allele-specific primer comprise target-specific sequence and tag units with a common sequence and a discriminating sequence so that the sequence of said tag units is not complementary to said first or second variant;
b) performing a polymerase chain reaction comprising a sense primer, an anti-sense primer and competitive cDNA products obtained from step a) as templates, wherein said sense primer comprises a 3' sequence that is complementary to the sequence present in the extended part of the competitive cDNA products derived from both the first and second RNA variant, and said anti-sense primer comprises a 3' sequence that hybridizes to the sequence complementary to said discriminating sequence of said tag units of said first allele-specific primer to form a set or sample of amplicons;
c) comparing this set of amplicons to a control set of amplicons (such as, for example, amplicon derived from both RNA variants of target sequence or from one or several reference genes) to quantitate first RNA variant in the sample comprising second RNA variant of target sequence.

Figure 1C:
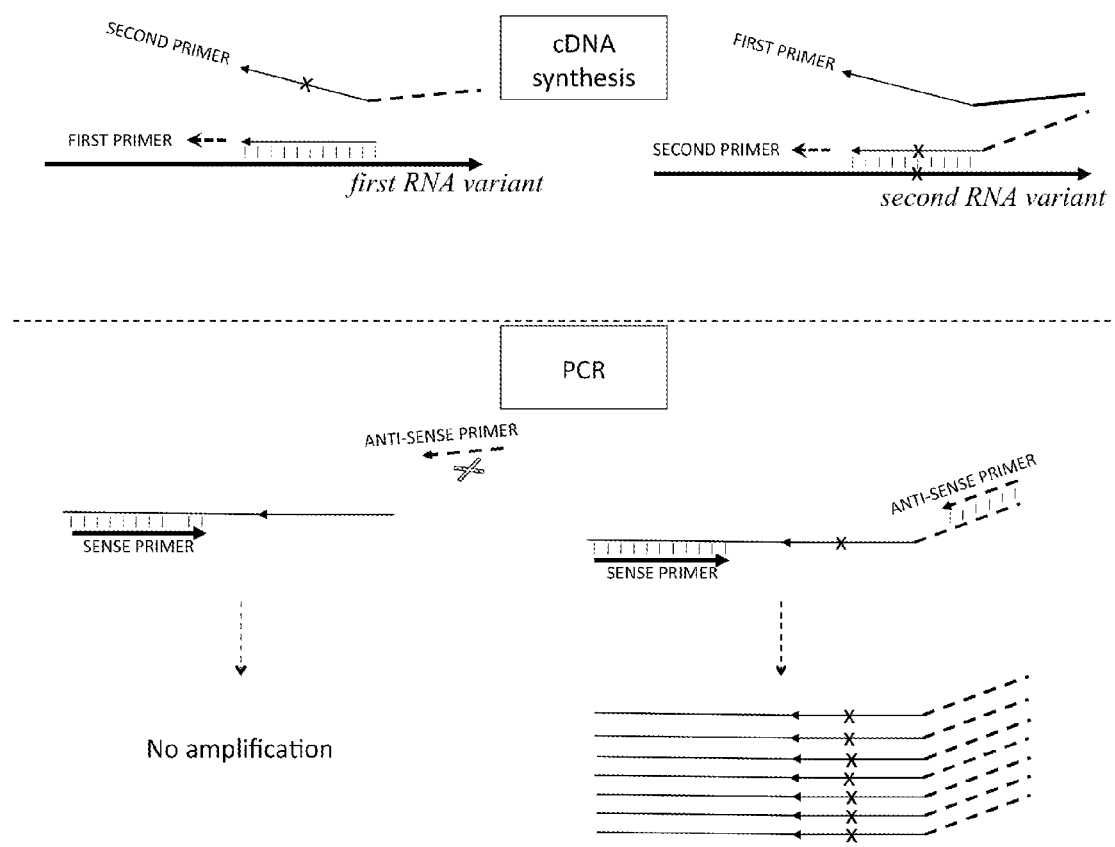
FIG. 1C: In one exemplary detectable amplification step, only competitive cDNA products derived from the second RNA variant is amplified with a common sense primer functioning in concert with an anti-sense primer that is complementary to the complement of the discriminating sequence of second primer.

Another embodiment of the invention is a method for the detection of the presence of RNA variants in a sample containing RNA, which is suspected to comprise one or more RNA variants of a gene of interest, wherein the method comprises the steps of:

a) performing a competitive cDNA synthesis comprising a first primer specific to a first RNA variant, a second primer specific to a second RNA variant, an RNA dependent DNA polymerase, and RNA, such as mRNA or viral genome RNA, from said sample as a template, wherein said first primer and said second primer comprise allele-specific nucleotide portion, target-specific sequence and tag units with a discriminating sequence so that the sequence of said tag units is not complementary to said first or second RNA variant, wherein each of the cDNA products obtained from said competitive cDNA synthesis consists of the sequence of only one primer extended by the sequence complementary to one of the target RNA variants;
b) performing a polymerase chain reaction comprising a sense primer, an anti-sense primer and the competitive cDNA products obtained from step a) as templates, wherein said sense primer comprises a 3' sequence that is complementary to the sequence present in the extended part of the competitive cDNA products derived from both the first and second RNA variant, and said anti-sense primer comprises a 3' sequence that hybridizes to the sequence complementary to said discriminating sequence of said tag units of said first allele-specific primer, so that the competitive cDNA products derived from the first RNA variant are amplified and the competitive cDNA products derived from the second RNA variant are not amplified (see FIG. 1C);

c) detecting the presence of polymerase chain reaction products obtained from step b), wherein the presence of said polymerase chain reaction products confirms that said first RNA variant is present in said sample.

Another embodiment of the invention is a method for the simultaneous detection of the presence of different RNA variants in a sample containing RNA, which is suspected to comprise one or more variants of a target sequence of interest, the method comprising the steps of:
a) performing a competitive cDNA synthesis comprising a first primer specific to a first RNA variant, a second primer specific to a second RNA variant, an RNA-dependent DNA polymerase, and RNA from said sample as a template, wherein said first primer and said second primer comprise an allele-specific nucleotide, a target-specific sequence and tag units with a common sequence and a discriminating sequence so that the sequence of said tag units is not complementary to said first or second RNA variant, wherein each of the cDNA products obtained from said competitive cDNA synthesis consists of the sequence of only one primer extended by the sequence complementary to one of the target RNA variants;
b) performing a polymerase chain reaction comprising a sense primer, an anti-sense primer and competitive cDNA products obtained from step a) as templates, wherein said sense primer comprises a 3' sequence that is complementary to the sequence present in the extended part of the competitive cDNA products derived from both the first and second RNA variant, and said anti-sense primer comprises a 3' sequence that is complementary to the complement of common sequence of said tag units, and wherein said polymerase chain reaction is performed so that the discriminating sequences of the tag units are also amplified;
c) detecting the presence of polymerase chain reaction products corresponding to the first and second RNA variant obtained from step b) utilizing the presence of the discriminating sequence of said tag units in said polymerase chain reaction products.

The above method is advantageous for detecting and/or quantitating first RNA variant (for example, a rare RNA variant) of a target sequence in a sample suspected of comprising at least a second RNA variant (for example, an abundant RNA variant) of a target sequence, particularly when said competitive cDNA synthesis of step a) comprises a third primer specific to the second RNA variant, wherein said third primer comprises the same or similar allele-specific nucleotide portion and target-specific sequence as the second primer but does not comprise tag units with the common sequence as in the first and second primer. In a preferred embodiment, the molar amount of said third primer in said competitive cDNA synthesis is higher than the molar amount of said second primer. For instance, the molar amount of said third primer in said competitive cDNA synthesis can be at least double compared to the molar amount of said second primer. The molar ratio of the second and the third primer can be 1:1, 1:2, 1:3, 1:4, 1:5, 1:6, 1:7, 1:8, 1:9, 1:10 or more.

Accordingly, one of the preferred embodiments of the invention is the following: In step a) of the method, a first reaction mixture is formed by combining the following: (i) an RNA sample; (ii) a first allele-specific primer, wherein an allele-specific nucleotide portion of the first allele-specific primer is fully complementary to the first RNA variant of the target sequence; (iii) a first form and second form of second allele-specific primer, wherein an allele-specific nucleotide portion of the second allele-specific primers is fully complementary to the second RNA variant of the target sequence (see FIG. 1E). Subsequently, a competitive cDNA synthesis is carried out to produce competitive cDNA products. Then, the effective concentration of unhybridized competitive allele-specific primers may be reduced in said competitive extension reaction before forming a second reaction mixture in step b) by combining (i) said competitive cDNA products; (ii) a common locus-specific primer comprises a 3' sequence that is complementary to competitive cDNA products derived from different RNA variants; (iii) a differential primer that functions in concert with common locus-specific primer in a PCR reaction to selectively amplify competitive cDNA products derived from the first allele-specific primer and the first form of second allele-specific primer; and preferably (iv) a detector probe. Next, an amplification reaction, typically a PCR amplification reaction, is carried out on the second reaction mixture, to form a first set and second set of amplicons. The first and second sets of amplicons are detected by a change in a detectable property of the detector probe or by other methods. Finally, the changes in the detectable property of the first set of amplicons and those of the second set of amplicons are compared.

In another embodiment, the present invention provides methods for selective amplification of only one group of RNA variant (such as, for example, one RNA variant) of target sequence. Some of these methods can include in step a): (i) hybridizing a first allele-specific primer to a sequence comprising first RNA variant of target sequence; (ii) hybridizing a second allele-specific primer to a sequence comprising second RNA variant of target sequence; (ii) competitively extending of both first and second allele-specific primer from sequence comprising first and second RNA variants, respectively, to form competitive cDNA products; and preferably reducing in said competitive cDNA synthesis the effective concentration of competitive allele-specific primers which have not formed part of said competitive cDNA products and which are in a form capable of producing a competitive cDNA products with said target sequence and/or the complementary sequence of said competitive cDNA products; and in step b) subjecting said competitive cDNA products to reagents and conditions sufficient for amplification of said competitive cDNA product derived from the said first allele-specific primer.

In another aspect, the present invention provides methods for competitive co-amplification of certain proportions of each RNA variant of a target sequence, such as, for example, the first RNA variant (for example, a rare RNA variant) and a portion of second RNA variant for example, an abundant RNA variant) of target sequence. Some of these methods can include in step a): (i) hybridizing a first allele-specific primer to a sequence comprising first RNA variant of target sequence; (ii) hybridizing the first form and second form of second allele-specific primer to a sequence comprising second RNA variant of target sequence; (iii) competitively extending of both first and second allele-specific primer from sequence comprising first and second RNA variants, respectively, to form competitive cDNA products; and preferably reducing in said competitive extension reaction the effective concentration of competitive allele-specific primers which have not formed part of said competitive cDNA products and which are in a form capable of producing a competitive cDNA products with said target sequence and/or the complementary sequence of said competitive cDNA products; and in step b) subjecting said competitive cDNA products to reagents and conditions sufficient for an amplification reaction of said competitive cDNA product derived from said first allele-specific primers and the first form of second allele-specific primer.

In another preferred embodiment of the invention, the amplification reaction of step b) is performed with a detector probe comprising the discriminating sequence of the first or second primer or a sequence complementary to said discriminating sequence. A detector probe specific to discriminating sequence of the first primer will specifically hybridize with the PCR products derived from the first RNA variant. A detector probe specific to discriminating sequence of the second primer will specifically hybridize with the PCR products derived from the second RNA variant.

In another preferred embodiment of the invention, the step c) of the above-mentioned method is performed by analyzing the melting profile of said polymerase chain reaction products, wherein the melting profile differs between the polymerase chain reaction products corresponding to the first and second RNA variant, and wherein this difference in the melting profile is due to the difference in the discriminating sequence of said tag units in addition to the difference between the RNA variants.

Competitive Allele-Specific Primers (CAPs)

Competitive allele-specific primers (CAPs) with low Tms exhibit increased discrimination of different RNA variants. In some embodiments, CAPs are oligonucleotide ranging from about 5-100, such as about 6-40, about 7-38, about 8-35, or about 9-30, or any range in between, nucleotides in length. In some embodiments, the Tm of CAPs ranges from about 4° C. to 80° C., such as about 10° C. to 68° C., about 37° C. to 66° C., about 42° C. to 64° C., about 48° C. to 62° C., or any temperature in between (e.g., 37° C., 48° C., 55° C., 56° C.). In other embodiments, the Tm of the CAPs is about 3° C. to 6° C. higher than the anneal/extend temperature of competitive cDNA synthesis.

In some embodiments of the disclosed compositions, the concentration of CAPs ranges from about 20 nM to 1000 nM, such as about 50 nM to 700 nM, about 100 nM to 500 nM, about 200 nM to 300 nM, about 400 nM to 500 nM, or any range in between. In some exemplary embodiments, the concentration of CAPs is between about 100 nM to 400 nM.

CAPs comprise an allele-specific nucleotide portion that is specific to the target RNA variant of interest. The allele-specific nucleotide portion of a CAP is complementary to one RNA variant of a target sequence, but not to alternative RNA variant of the target sequence. In other words, the allele-specific nucleotide portion binds to one or more variable nucleotide positions that are known to contain different nucleotides for different RNA variant of a target sequence. The allele-specific nucleotide portion is at least one nucleotide in length. In exemplary embodiments, the allele-specific nucleotide portion is one nucleotide in length. In some embodiments, the allele-specific nucleotide portion of an allele-specific primer is located at the 3' terminus of the competitive allele-specific primer. In other embodiments, the allele-specific nucleotide portion is located about 1-2, 3-4, 5-6, 7-8, 9-11, 12-15, or 16-20 nucleotides in from the 3'most-end of the competitive allele-specific primer. In further embodiments, the allele-specific nucleotide portion is situated around the centre of allele-specific priming sequence of competitive allele-specific primer.

The allele-specific primer also comprises a target-specific portion that is specific to the target sequence. In some embodiments the target-specific portion is about 75-85%, 85-95%, 95-99% or 100% complementary to the target sequence of interest. The target-specific portion of the allele-specific primer also comprises the allele-specific nucleotide portion. In other embodiments, the target-specific portion is located 5' to the allele-specific nucleotide portion. The target-specific portion can be about 4-30, about 5-25, about 6-20, about 7-15, or about 8-10 nucleotides in length. In some embodiments, the Tm of the target specific portion is about 5° C. above the annealing/extension temperature used for competitive cDNA synthesis. In some embodiments, the Tm of the target specific portion of the allele-specific primer ranges from about 4° C. to 80° C., such as about 10° C. to 68° C., about 37° C. to 66° C., about 42° C. to 64° C., about 48° C. to 62° C., or any temperature in between (e.g., 37° C., 48° C., 55° C., 56° C.).

In some embodiments of the disclosed methods and kits, the target-specific portion of the first competitive allele-specific primer and the target-specific portion of the second competitive allele-specific primer comprise the same sequence. In other embodiments, the target-specific portion of the first allele-specific primer and the target-specific portion of the second allele-specific primer are not identical sequences.

In some embodiments, the allele-specific primer can comprise a tag unit or tag units. In some embodiments, the tag units are located 5' to the target-specific portion of CAPs. In some embodiments, the tag units are located inside the target specific portion of CAPs. In some embodiments, the tag units are located at both said regions. In some embodiments, the number of tag units can be about 0-100, such as about 4-60, about 8-50, about 16-40, about 20-30, or about 22-28 nucleotides in length.

In some embodiments, several adjacent tag units form a GC-rich region. For example, in some embodiments, the GC-rich region of adjacent tag unit is comprised of about 50-100%, about 60-100%, about 70-100%, about 80-100%, about 90-100% or about 95-100% G and/or C nucleotides. In some embodiments, several adjacent tag units form an AT-rich region. For example, in some embodiments, the AT-rich region of adjacent tag unit is comprised of about 50-100%, about 60-100%, about 70-100%, about 80-100%, about 90-100% or about 95-100% A and/or T nucleotides.

Kits and Compositions

In another embodiment, the present invention provides a kit for the detection of the presence of RNA variants in a sample comprising nucleic acids, the kit comprising one primer specific to a first RNA variant, and one or two primers specific to a second RNA variant, wherein the primer specific to a first RNA variant and at least one of the primers specific to a second RNA variant comprise tag units with a common sequence and a discriminating sequence so that the sequence of said tag units is not complementary to said first or second RNA variant. Said tag units may form a 5' nucleotide tail in the primers. The discriminating sequence of said tag units in one of the two primers specific to the first RNA variant can form a GC-rich region and the discriminating sequence of said tag units in the primer specific to the second RNA variant can form an AT-rich region.

Preferably, said kit further comprises a primer pair consisting of a sense primer and an anti-sense primer, wherein said sense primer comprises a 3' sequence that is complementary to the sequence present in the extended part of the competitive cDNA products derived from both the first and second RNA variant, and said anti-sense primer comprises a 3' sequence that hybridizes to the sequence complementary to the common sequence of said tag units.

The kit of the present invention may further comprise a RNA-dependent DNA polymerase.

In another embodiment, the present invention provides a kit for the detection of the presence of RNA variants in a sample comprising RNA, wherein the kit comprises one primer specific to a first RNA variant, and one primer specific to a second RNA variant, wherein the two primers comprise target-specific sequence, allele-specific nucleotide portion and tag units with a discriminating sequence so that the sequence of said tag units is not complementary to said first or second RNA variant. This kit may further comprise a primer pair consisting of a sense primer and an anti-sense primer, wherein said sense primer comprises a 3' sequence that is complementary to a sequence present in the extended part of the competitive cDNA products derived from both the first and second RNA variants, and said anti-sense primer hybridizes to the sequence complementary to said discriminating sequence in one of the two primers.

The present invention also provides a composition for a competitive cDNA synthesis comprising only one primer specific to a first RNA variant and up to two primers specific to a second RNA variant, wherein the primer specific to a first RNA variant and at least one of the primers specific to a second RNA variant comprise tag units, preferably in a form of a 5' nucleotide tail, with a common sequence and a discriminating sequence so that the sequence of said tag units is not complementary to said first or second RNA variant. The composition may further comprise template RNA suspected to comprise one or more RNA variants of a sequence of interest. Preferably, the composition further comprises an RNA-dependent polymerase, when the template nucleic acid is RNA such as mRNA or viral genome RNA.

The present invention also provides another composition for a competitive cDNA synthesis comprising only one primer specific to a first RNA variant and only one primer specific to a second RNA variant, wherein the two primers comprise target-specific sequence, allele-specific nucleotide portion and tag units with a discriminating sequence so that the sequence of said tag units is not complementary to said first or second RNA variant. Also this composition may further comprise template nucleic acid suspected to comprise one or more RNA variants of a gene of interest. Preferably, the composition further comprises a RNA-dependent polymerase, when the template nucleic acid is RNA such as mRNA or viral genome RNA.

In one aspect, the present invention provides compositions for use in identifying and/or quantifying different RNA variants of a target sequence in a nucleic acid sample. Some of these compositions can comprise: (a) competitive allele-specific primers; (b) a common locus-specific primer (c) a detector probe; and (d) a differential primer, or any combinations thereof. In some embodiments of the compositions, the compositions may further comprise a polymerase, dNTPs or NTP, reagents and/or buffers suitable for cDNA synthesis and PCR amplification or other amplification methods, and/or a template sequence or nucleic acid sample. In some embodiments, the polymerase can be thermostable.

In another aspect, the invention provides compositions comprising: (i) a first competitive allele-specific primer, wherein an allele-specific nucleotide portion of the first competitive allele-specific primer is complementary to the first RNA variant of a target sequence; and (ii) a second competitive allele-specific primer, wherein an allele-specific nucleotide portion of the second competitive allele-specific primer is complementary to the second RNA variant of a target sequence.

In some illustrative embodiments, the compositions can further include a common locus-specific primer that is complementary to sequence present in the extended part of the competitive cDNA products derived from both the first and second RNA variant and a differential primer that functions in concert with the locus-specific primer in a PCR reaction to selectively amplify one competitive cDNA product or to co-amplify a group of competitive cDNA products.

In further embodiments, the compositions can further include a detector probe.

EXAMPLES

I. ART-PCR Assay Designs

In general, an ART-PCR assay includes a cDNA synthesis reaction followed by a quantitative polymerase chain reaction (qPCR). For each SNP that was analyzed, a pair of competitive allele-specific primers was designed to target the first RNA variant (first primer) and the second RNA variant (second primer) during cDNA synthesis. Both first primer and second primer are included in the cDNA synthesis reaction of ART-PCR assay to competitively initiate the synthesis of cDNA on corresponding RNA templates. In the following step, either one or both cDNA products were amplified by a detectable amplification method, such as qPCR. Different schemas for ART-PCR assays used in the following examples are illustrated in either FIG. 1C, 1D, 1E or 1F:

In an ART-PCR assay for second RNA variant analysis, the cDNA synthesis reaction mixture includes a first primer without tag units and a second primer with tag units (FIG. 1C).

Figure 1D:
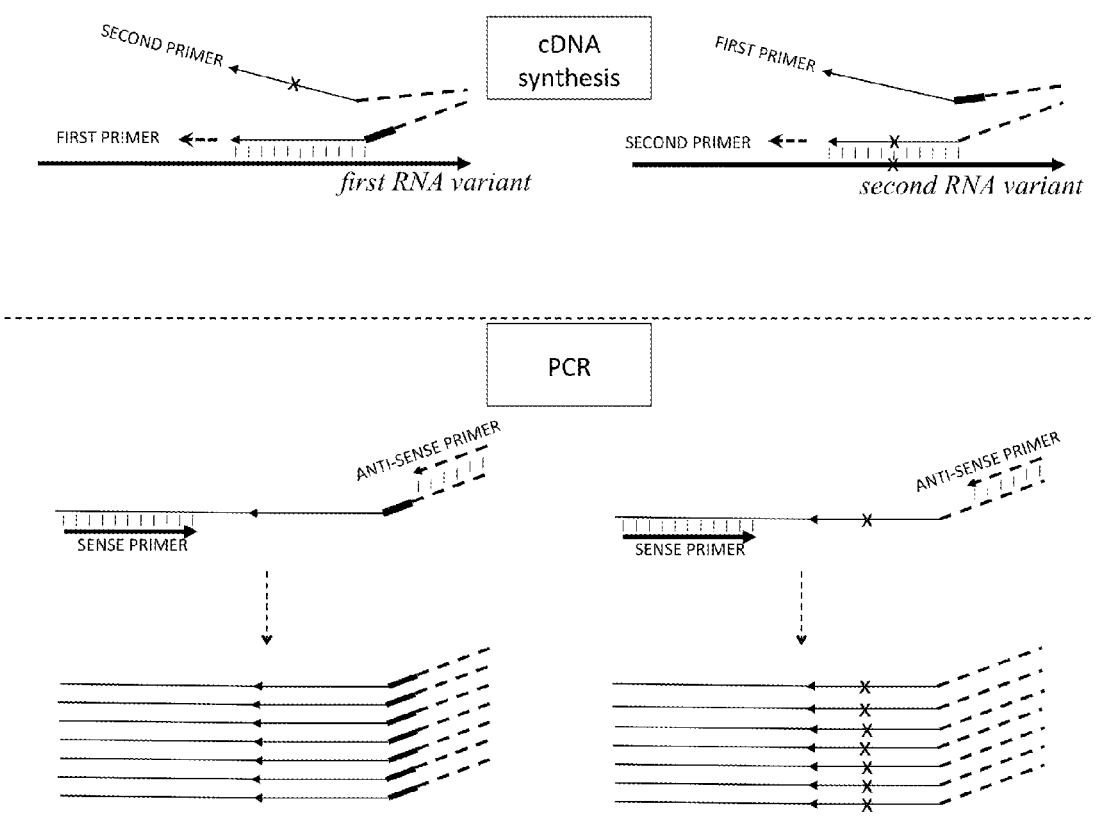
FIG. 1D: In another exemplary detectable amplification step, both competitive cDNA products are competitively co-amplified. The discriminating sequences are situated between the priming sites of sense and anti-sense primer on each competitive cDNA product. As a result, the discriminating sequences are also amplified, and the amplification products are readily detected and discriminated, utilizing these discriminating sequences.

In an ART-PCR assay for simultaneous analysis of first RNA variant and second RNA variant, the cDNA synthesis reaction mixture includes a first primer and a second primer, wherein both primers comprise tag units with a common sequence and a discriminating sequence (FIG. 1D).

Figure 1E:
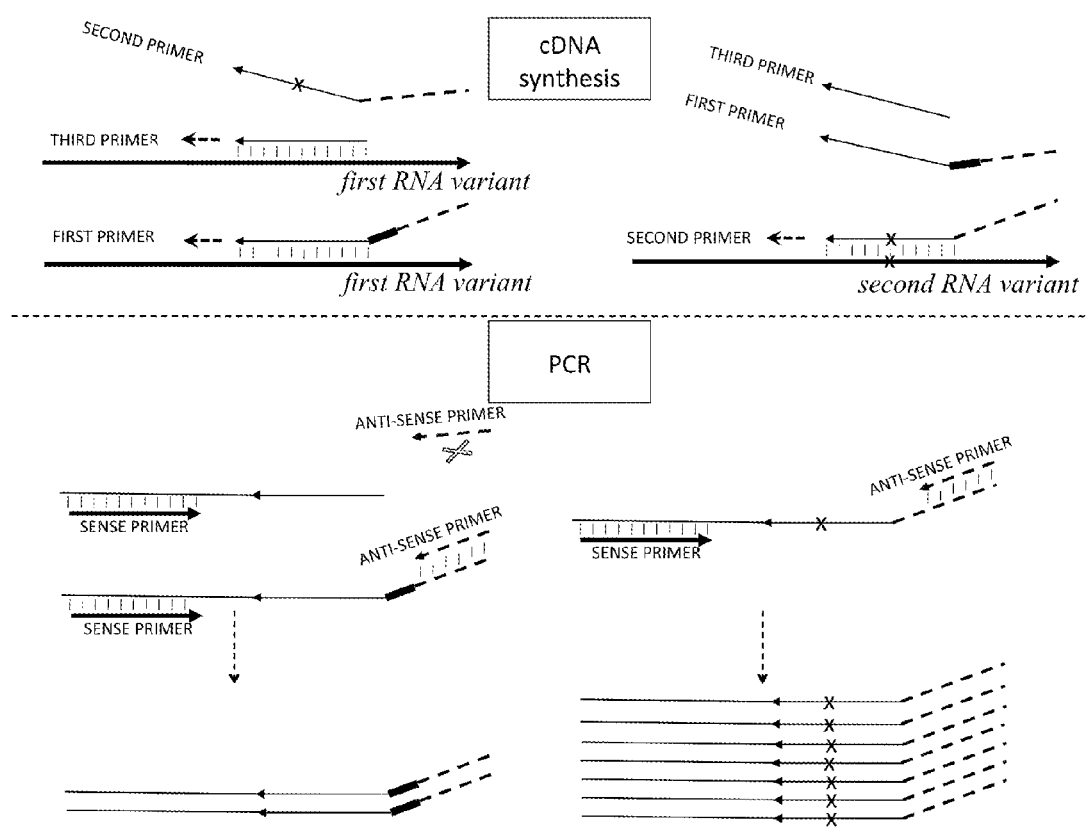
FIG. 1E: In a further exemplary detectable amplification step, the competitive cDNA product derived from the second RNA variant and only a portion of competitive cDNA products derived from the first RNA variant are competitively co-amplified. The remaining competitive cDNA product initiated by the third primer annealed to the first RNA variant is not amplifiable under condition of this amplification reaction, as a result of, for example, lacking priming site for the selective anti-sense primer. Consequently, the RT-PCR product of the second variant is enriched in comparison to that of the first variant.

In an ART-PCR assay that enables enrichment of the second RNA variant (for example, a rare variant) and simultaneous analysis of both RNA variants, the cDNA synthesis reaction mixture includes a first primer and a second primer, wherein both primers comprise tag units with a common sequence and a discriminating sequence. The cDNA synthesis reaction mixture further includes a third primer targeting the first RNA variant as the first primer, but the third primer does not comprise tag units (FIG. 1E).

Figure 1F:
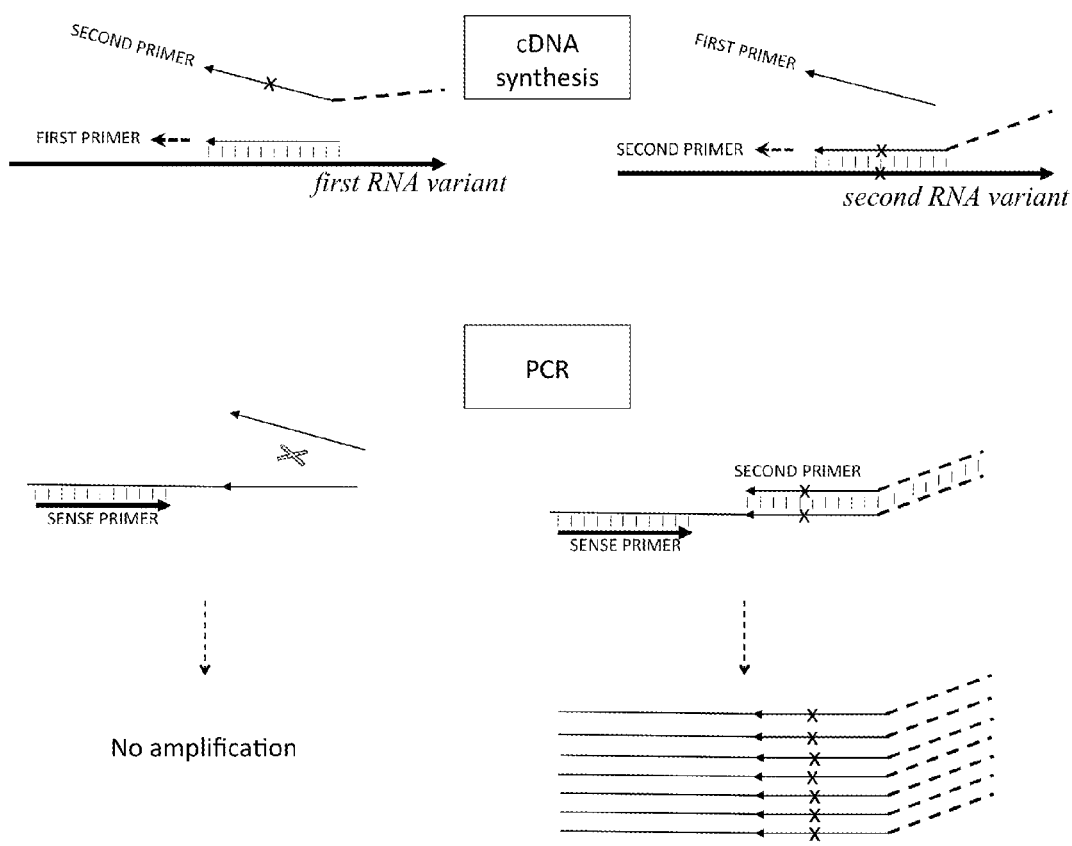
FIG. 1F: The cDNA synthesis and PCR of ART-PCR assay can be performed in a single tube. For analysis of the second variant, the ART-PCR reaction mixture includes a first primer without tag units, a second primer with tag units, and a common locus-specific sense primer (FIG. 1F). In the first step of cDNA synthesis, the first primer and the second primer compete successfully to initiate cDNA synthesis on first and second RNA variants, respectively. In the following PCR step, the second primer will be the anti-sense primer that functions in concert with the common locus-specific sense primer to PCR amplify the cDNA product resulted from the second primer. The cDNA product resulted from the first primer is not amplified because PCR was performed with an annealing temperature higher than the melting temperature of the first primer.

For analysis of a second RNA variant using an ART-PCR assay in a single tube, the ART-PCR reaction mixture includes a first primer without tag units, a second primer with tag units, and a common locus-specific sense primer (FIG. 1F). In the first step of cDNA synthesis, the first primer and the second primer compete successfully to initiate cDNA synthesis on first and second RNA variant, respectively. In the following PCR step, the second primer will be the anti-sense primer that function in concert with the common locus-specific sense primer to PCR amplify the cDNA product resulted from the second primer. The cDNA product resulted from the first primer is not amplified because PCR was performed with an annealing temperature higher than the melting temperature of the first primer.

II. RNA Samples

We obtained DNA oligos of which the sequences correspond to wildtype and different mutations of KRAS gene and BRAF gene from TAG Copenhagen A/S. Each oligo is 100 nucleotides in length, including 20 nucleotides of T7 promoter's sequence at the 5' end. Using the synthetic DNA oligos as templates, we prepared corresponding PCR products and generated RNA by in vitro transcription with AmpliScribe™ T7, T3, and SP6 High Yield Transcription Kits (EPICENTRE Biotechnologies) according to manufacturer's instruction. The resulted RNA samples were quantified using Realtime RT-PCR with SYBR Green (Tetro cDNA synthesis kit and SensiFAST™ SYBR No-ROX Kit, Bioline) according to manufacturer's instruction and were used to validated the sensitivity, specificity of given ART-PCR assays.

III. Reaction Conditions

III.1. CDNA Synthesis:

All components of the cDNA synthesis reactions except the enzyme Tetro Reverse Transcriptase (Bioline) were assembled to form 10-uL cDNA synthesis reactions. The reactions were incubated at 65° C. for 5', then cooled down to 50° C. before adding the enzyme Tetro Reverse Transcriptase to each well. Afterward, the reaction temperature was decreased 1° C. every 1' from 50° C. to 37°, then increased to 85° C. for 5' to inactivate the Reverse Transcriptase. Reverse-transcription products were stored at −20° C. for later analysis.

III.2. Quantitative PCR:

An 1-uL aliquot of each cDNA synthesis products was used as template in the following 10 uL-qPCR reaction (SensiFAST™ SYBR No-ROX Kit, Bioline or SensiFAST™ Probe No-ROX Kit, Bioline for probe-based detection). The PCR reactions were incubated in a 384-well plate at 95° C. for 2 minutes, then for 45 (SYBR Green detection) or 50 cycles (Taqman probe) at 95° C. for 5 seconds, 58° C. for 10 seconds and 68° C. for 10 seconds. All reactions were run in duplicate or higher replication in a LighCycler 480 Real-Time PCR System. Subsequent to PCR reaction using SensiFAST™ SYBR No-ROX Kit, the melting analyses were performed from 58° C. to 95° C., 0.2° C. interval.

III.3. Quantitative One-Step RT-PCR:

One-Step RT-PCR were performed on the Pikoreal cycler using an iScript™ One-Step RT-PCR Kit with SYBR® Green (Biorad). All components of the reaction except the enzyme reverse transcriptase were incubated 65° C. for 5', then cooled down to 50° C. before adding the enzyme iScript Reverse Transcriptase. After adding the enzyme, the temperature of the reaction was decreased 1° C. every 1' from 50° C. to 37°, then increased to 95° C. for 5' to inactivate the enzyme reverse transcriptase before proceeding to PCR program with 50 cycles at 95° C. for 10 seconds, 58° C. for 10 seconds and 68° C. for 20 seconds.

IV. Data Analysis

Threshold cycle (Ct) was calculated automatically using the second derivative maximum method. The ΔCt between amplification reactions for matched vs. mismatched sequences is defined as the specificity of ART-PCR ($\Delta Ct = Ct_{matched} - Ct_{mismatched}$). The larger the ΔCt between mismatched and matched targets, the better assay specificity. The ΔCt value was used to estimate the power of discrimination (or selectivity) which is equal to $\frac{1}{2}^{\Delta Ct}$ or, in some cases, calculated as % ($\frac{1}{2}^{\Delta Ct} \times 100$).

Example 1: Competitive Allele-Specific Primer Suppresses Efficiently Mismatched Priming During cDNA Synthesis, while Non-Extendable Oligonucleotides of the Same Sequence do not This example showed that the extension of the first primer (specific to a first RNA variant) upon hybridization to the first RNA variant is critical for efficient suppression of nonspecific cDNA synthesis initiated by the second primer (specific to a second RNA variant) mis-annealed to the first RNA variant. (FIG. 1 C)

Materials:

```
Sequence of BRAF wildtype RNA (first variant):
                                     (SEQ ID NO: 1)
5'UGAAGACCUCACAGUAAAAAUAGGUGAUUUUGGUCUAGUACAGUGAAA

UCUCGAUGGAGUGGGUCCCAUCAGUUUGAAC 3'

Sequence of V600E BRAF mutant RNA (second variant):
                                     (SEQ ID NO: 2)
5'UGAAGACCUCACAGUAAAAAUAGGUGAUUUUGGUCUAGCUACAGAGAA

AUCUCGAUGGAGUGGGUCCCAUCAGUUUGAAC 3'

Wildtype-specific primer (first primer):
                                     (SEQ ID NO: 3)
5'AGATTTCACTGTAG 3'

Wildtype-specific oligo with PO4 group at the 3'
end (B-PO4):
                                     (SEQ ID NO: 4)
5'AGATTTCACTGTAG-PO4 3'

Wildtype-specific oligo with hexa-A tail at the 3'
end (B-Atail):
                                     (SEQ ID NO: 5)
5'AGATTTCACTGTAG-AAAAAA 3'

Mutation-specific primer (second primer):
                                     (SEQ ID NO: 6)
5'GCCGATCAGACGACGACTATTATTGATTTCTCTGTAG 3'

Anti-sense PCR primer:
                                     (SEQ ID NO: 7)
5' CGATCAGACGACGAC 3'

Sense PCR primer:
                                     (SEQ ID NO: 8)
5' AGACCTCACAGTAAAAATAGGTGA 3'
```

Method:

CDNA synthesis reactions containing the second primer (mutation-specific primer) were carried out in the absence or the presence of one wildtype-specific oligonucleotide, either the first primer (wildtype-specific primer), the wildtype-specific oligonucleotide with PO$_4$ group at the 3' end (B-PO$_4$), or the wildtype-specific oligonucleotide with a hexa-A tail at the 3' end (B-Atail). In addition to the priming sequence at the 3' end, the second primer also contains a tail of unrelated sequence at the 5' end (underlined sequence). The same copy number (10$^7$ copies) of the RNA template, either V600E BRAF mutant RNA (second variant) or BRAF wildtype RNA (first variant), was used in each reaction of cDNA synthesis. A 1 uL-aliquot of each cDNA synthesis products was used as template in the following 10 uL-qPCR reactions with the sense PCR primer and the anti-sense PCR primers indicated above. While these PCR reactions will amplify the cDNA products resulted from the second primer, the cDNA product resulted from the first primer will not be amplified due to lacking the priming site for the anti-sense PCR primer. Consequently, the amplification curve (or Ct value) resulted from the second variant RNA template represents the correct priming event, while the Ct value of amplification curve resulted from the first variant RNA template represent the mis-matched priming event of the second primer. The difference between those two Ct values (ΔCt) corresponds to the efficiencies of mismatched priming of the second primer to the first variant RNA template during cDNA synthesis.

Figure 2A:
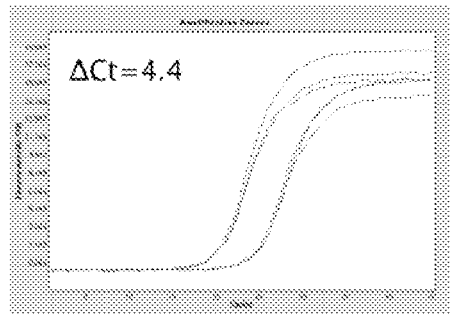
FIG. 2 shows the improved specificity of cDNA synthesis in the presence of competitive allele-specific primers in comparison to different non-extendable competitive oligonucleotides and reactions without competitive oligonucleotides or primers.
Figure 2B:
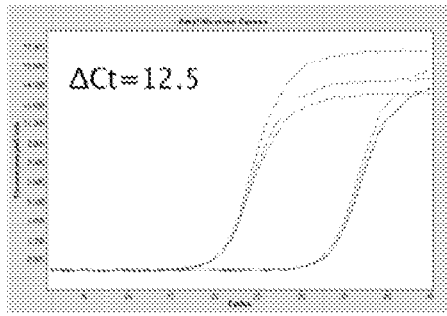
Figure 2C:
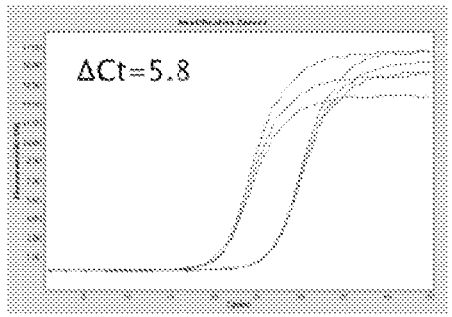
Figure 2D:
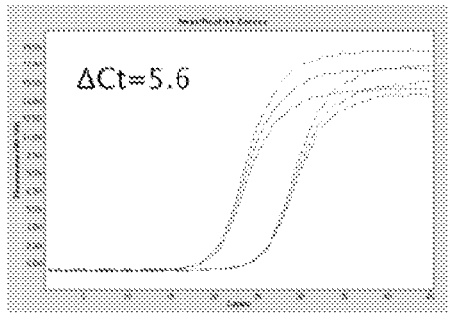

Result:

The mis-priming efficiency in the cDNA synthesis reaction containing only the second primer is quite high, as indicated by the delay in the Ct value (ΔCt) of only 4.4 cycles (FIG. 2A). This ΔCt value corresponds to a mis-priming efficiency that accounts for about 5% ($=\frac{1}{2}^{4.4}$) of the correct priming efficiency. However, the mis-priming efficiency drops tremendously in the cDNA synthesis reaction containing both the second primer and the first primer, as indicated by the ΔCt value of 12.5 cycles (FIG. 2B). This ΔCt value corresponds to a mis-priming efficiency that accounts for 0.017% ($=\frac{1}{2}^{12.5}$) of the correct priming efficiency.

When the cDNA synthesis reactions were performed in the presence of non-extendable oligonucleotides with the same sequence as the first primer, the ΔCt values were 5.8 and 5.6 (FIGS. 2B&C) for the B-PO4 primer and the B-Atail primer, respectively. These ΔCt values correspond to mis-priming levels that account for 1.8% and 2.1% of the correct priming efficiencies.

Example 2: Determination of the Specificity of ART-PCR

In this example, the specificity of ART-PCR assays for detection of different mutations on codon 12 of KRAS transcripts was determined by comparing the amplification curves derived from correct priming (using mutant RNA template) and mismatched priming events (using wildtype RNA template) during cDNA synthesis reaction in the presence of the competitive wildtype-specific primer. (FIG. 1C)

Materials:

```
Sequence of KRAS wildtype RNA (first variant):
                                          (SEQ ID NO: 9)
5'AUGACUGAAAAUGACUGAAUAUAAACUUGUGGUAGUUGGAGCUGGUGG

CGUAGGCAAGAGUGCCUUGACGA 3'

Sequences of KRAS mutant RNAs (second variants)
with the mutation sites in bold and highlighted:
M₁. KRAS-12/Asp (GGT>GAT):
                                          (SEQ ID NO: 10)
5' AUGACUGAAAAUGACUGAAUAUAAACUUGUGGUAGUUGGAGCUGAUG

GCGUAGGCAAGAGUGCCUUGACGA 3'

M₂. KRAS-12/Ala (GGT>GCT):
                                          (SEQ ID NO: 11)
5' AUGACUGAAAAUGACUGAAUAUAAACUUGUGGUAGUUGGAGCUGCUG

GCGUAGGCAAGAGUGCCUUGACGA 3'

M₃. KRAS-12/Val (GGT>GTT):
                                          (SEQ ID NO: 12)
5' AUGACUGAAAAUGACUGAAUAUAAACUUGUGGUAGUUGGAGCUGUUG

GCGUAGGCAAGAGUGCCUUGACGA 3'

M₄. KRAS-12/Ser (GGT>AGT):
                                          (SEQ ID NO: 13)
5' AUGACUGAAAAUGACUGAAUAUAAACUUGUGGUAGUUGGAGCUAGUG

GCGUAGGCAAGAGUGCCUUGACGA 3'

M₅. KRAS-12/Arg (GGT>CGT):
                                          (SEQ ID NO: 14)
5' AUGACUGAAAAUGACUGAAUAUAAACUUGUGGUAGUUGGAGCUCGUG

GCGUAGGCAAGAGUGCCUUGACGA 3'

M₆. KRAS-12/Cys (GGT>TGT):
                                          (SEQ ID NO: 15)
5' AUGACUGAAAAUGACUGAAUAUAAACUUGUGGUAGUUGGAGCUTGUG

GCGUAGGCAAGAGUGCCUUGACGA 3'

Wildtype-specific primer (first primer):
                                          (SEQ ID NO: 16)
5' GCCACCAGCT 3'

Mutation-specific primers (second primer):
S₁. Primer KRAS-12/Asp:
                                          (SEQ ID NO: 17)
5'GCCGATCAGACGACGACTATTATTCCATCAGCT 3'

S₂. Primer KRAS-12/Ala:
                                          (SEQ ID NO: 18)
5'GCCGATCAGACGACGACTATTATTCCAGCAGC 3'

S₃. Primer KRAS-12/Val:
                                          (SEQ ID NO: 19)
5'GCCGATCAGACGACGACTATTATTCCAACAGCT 3'

S₄. Primer KRAS-12/Ser:
                                          (SEQ ID NO: 20)
5'GCCGATCAGACGACGACTATTATTCCACTAGCT 3'

S₅. Primer KRAS-12/Arg:
                                          (SEQ ID NO: 21)
5'GCCGATCAGACGACGACTATTATTCCACGAGC 3'

S₆. Primer KRAS-12/Cys:
                                          (SEQ ID NO: 22)
5'GCCGATCAGACGACGACTATTATTCCACAAGCT 3'

Anti-sense PCR primer:
                                          (SEQ ID NO: 23)
5' CGATCAGACGACGAC 3'

Sense PCR primer:
                                          (SEQ ID NO: 24)
5' TGACTGAATATAAACTTGTGGT 3'
```

Method:

Assays were performed using ART-PCR schema depicted in FIG. 1C with SYBR Green-based qPCR detection platform and reaction conditions indicated above using $10^7$ copies of either wildtype (first variant) or mutant KRAS RNA (second variant) as template.

In each ART-PCR assay for detection of the KRAS mutant RNA (second variant), which is denoted by $M_i$ (i=1, 2, ..., 6), the cDNA synthesis reaction mixture include the second primer $S_i$ (mutation-specific primer) with tag units and the first primer (wildtype-specific primer) without tag units.

Result:

The specificity of each assay calculated from the ΔCt value was shown in the FIG. 3.

Example 3: ART-PCR can Also be Performed Using Probe-Based Detection in PCR Step This example showed that ART-PCR assays could be performed using probe-based detection in PCR step. (FIG. 1C)

Materials:

```
Sequence of KRAS wildtype RNA (first variant):
                                    (SEQ ID NO: 25)
5' AUGACUGAAAAUGACUGAAUAUAAACUUGUGGUAGUUGGAGCUGGUG

GCGUAGGCAAGAGUGCCUUGACGA 3'

Sequences of KRAS mutant RNA (second variant)
with the mutation sites in bold and highlighted:
                                    (SEQ ID NO: 26)
5' AUGACUGAAAAUGACUGAAUAUAAACUUGUGGUAGUUGGAGCUCGUG

GCGUAGGCAAGAGUGCCUUGACGA 3'

Wildtype-specific primer:
                                    (SEQ ID NO: 27)
5' GCCACCAGCT 3'

Mutation-specific primers:
                                    (SEQ ID NO: 28)
5'GCCGATCAGACGACGACTATTATTCCACGAGC 3'

Anti-sense PCR primer:
                                    (SEQ ID NO: 29)
5' CGATCAGACGACGAC 3'

Sense PCR primer:
                                    (SEQ ID NO: 30)
5'TGACTGAATATAAACTTGTGGT3'

Probe sequence:
5' FAM-AT+TA+TT+CC+ACG+AG+CTCC-BQ1 3'
(+N: LNA nucleotide)
```

Method:

Assays were performed using ART-PCR schema depicted in FIG. 1C using $10^7$ copies of either KRAS wildtype (first variant) or KRAS mutant RNA (second variant) as template. The cDNA synthesis reactions, which contain both the second primer with tag units (mutation-specific primer) and the first primer without tag units (wildtype-specific primer) indicated above, were followed by probe-based qPCR detection using the SensiFAST™ Probe No-ROX Kit (Bioline). Due to the AT-rich nature, the probe sequence is designed to contain several LNA nucleotides with respect to increase its melting temperature.

Figure 4:
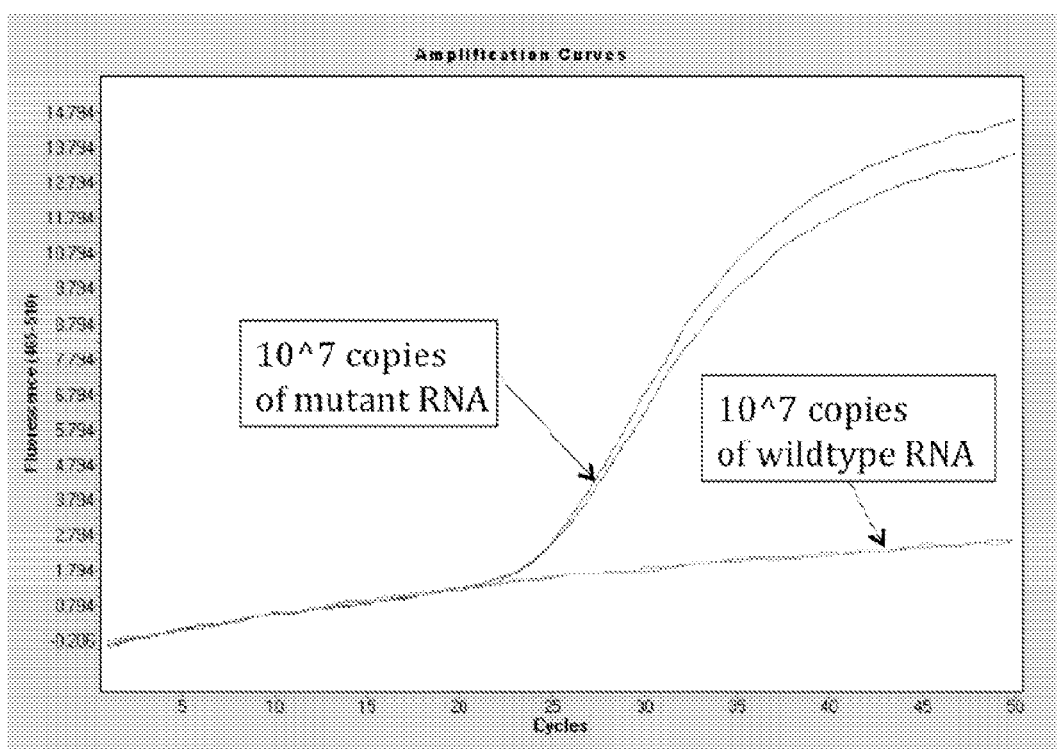
FIG. 4 depicts the specificity of detection of KRAS mutant RNA transcript using an ART-PCR assay with sequence-based detection in one exemplary embodiment.

Result:

Although the ART-PCR assay with first variant as RNA template ($10^7$ copies) generated amplification curves rising above the background level after about 20 cycles, there is no amplification signal after 50 PCR cycles (FIG. 4) when the second variant ($10^7$ copies) was used as template, indicating high specificity of the ART-PCR assay.

Example 4: Simultaneous Detection of Both Mutant and Wildtype RNA Variants in One Tube with ART-PCR This example showed that ART-PCR could be designed to co-amplify and simultaneously detect both the mutant and wildtype RNA transcripts in one PCR reaction. (FIG. 1 B)

Materials:

```
Sequence of KRAS wildtype RNA (first variant):
                                    (SEQ ID NO: 31)
AUGACUGAAAAUGACUGAAUAUAAACUUGUGGUAGUUGGAGCUGGUGGCG

UAGGCAAGAGUGCCUUGACGA

Sequence of KRAS mutant RNA (second variant):
                                    (SEQ ID NO: 32)
AUGACUGAAAAUGACUGAAUAUAAACUUGUGGUAGUUGGAGCUGCUGGCG

UAGGCAAGAGUGCCUUGACGA

Wildtype-specific primer (first primer):
                                    (SEQ ID NO: 33)
GCCGATCAGACGACGACCACCCTGCCACCAGC Mutation-specific primer (second primer):
                                    (SEQ ID NO: 34)
GCCGATCAGACGACGACTATTATTCCAGCAGC Anti-sense PCR primer:
                                    (SEQ ID NO: 35)
5' CGATCAGACGACGAC 3'

Sense PCR primer:
                                    (SEQ ID NO: 36)
5'TGACTGAATATAAACTTGTGGT 3'
```

Method:

Assays were performed according to ART-PCR schema depicted in FIG. 1D. cDNA synthesis were carried out in the presence of both the second primer (mutation-specific primer) and the first primer (wildtype-specific primer) indicated above, using a mixture of equal amounts ($10^7$ copies each) of KRAS mutant RNA (second variant) and KRAS wildtype RNA (first variant) as template. Both the second and first primer contain a 5' tail (tag units) of unrelated sequences, which comprises of a common sequence at the 5' end (highlighted) and a discriminating sequence (underlined) in the middle of each primer. Consequently, the cDNA products derived from these two primers will be co-amplified using the same PCR primer pair shown above, and the discriminating sequence will also be amplified. The discriminating sequences will form the basis to differentiate the mutant and wildtype RT-PCR products, for example, by using melting curve analysis or probe-based detection. In this example, the discriminating sequence of the second primer is designed to be AT-rich and that of the first primer is designed to be GC-rich. As a result, the RT-PCR products derived from second variant will have a significantly lower melting temperature than the RT-PCR products derived from first variants. Accordingly, those two RT-PCR products can be discriminated using melting curve analysis.

Figure 5:
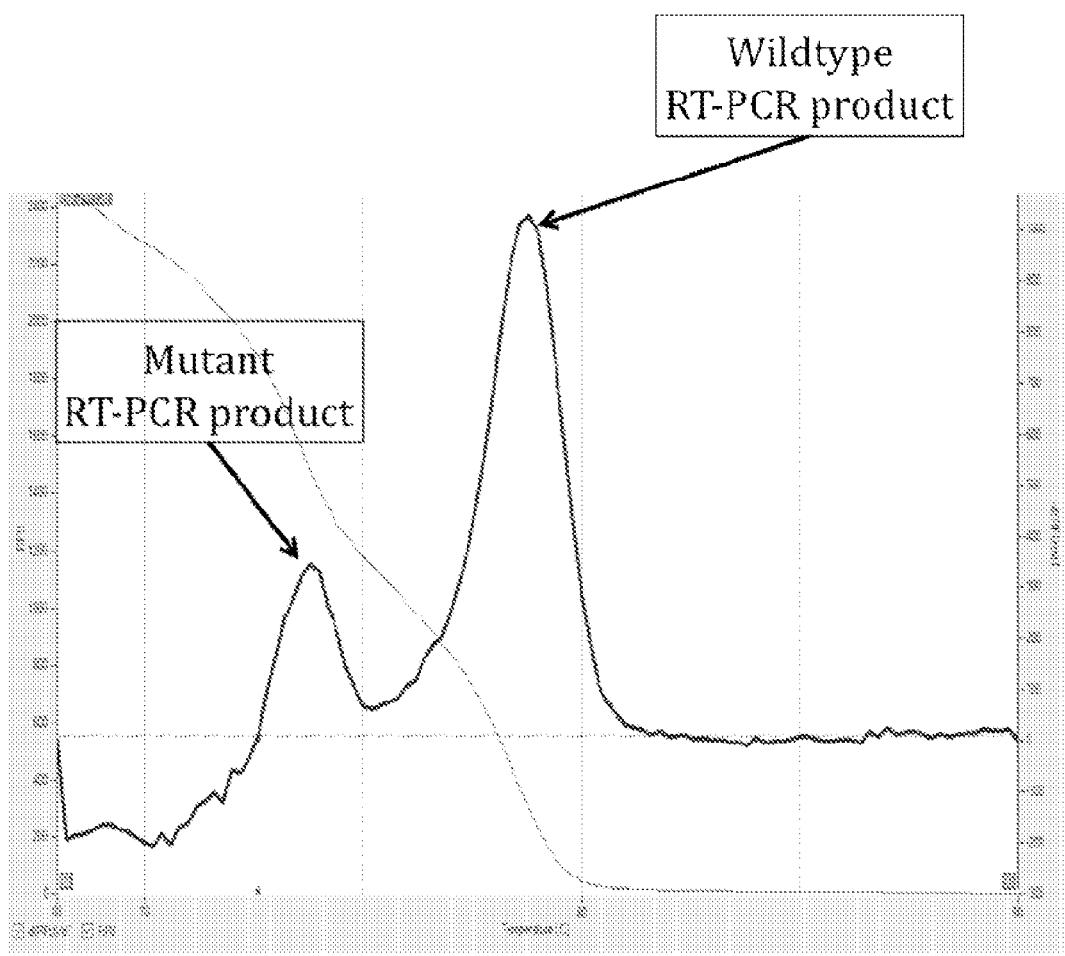
FIG. 5 depicts simultaneous amplification and detection of RT-PCR products derived from both RNA variants in one PCR tube using an ART-PCR assay in one exemplary embodiment.

Results:

The melting curve derived from one PCR reaction reveals two melting peaks (FIG. 5), one peak at around 74° C. representing the RT-PCR product resulted from the second variant and another peak at around 79° C. representing the RT-PCR product resulted from the first variant.

Example 5: Combining Two Forms of an Allele-Specific Primer in a cDNA Synthesis Reaction can Control the Amount of RT-PCR Products Resulted from an Abundant RNA Variant This example showed, in principle, that ART-PCR could be designed to inhibit the amplification of an abundant RNA variant, thus enriching the RT-PCR product resulted from the rare RNA variant. In particular, cDNA synthesis reaction mixture comprises two primers specific to the abundant RNA variant, one primer with tag units at lower molar concentration and the other without tag units at higher molar concentration.

Materials:

Sequence of KRAS wildtype RNA:
(SEQ ID NO: 37)
AUGACUGAAAAUGACUGAAUAUAAACUUGUGGUAGUUGGAGCUGGUGGCG
UAGGCAAGAGUGCCUUGACGA (SEQ ID NO: 38)
Wildtype-specific primer with tag units: GCCGATCAGACGACGACCACCCTGCCACCAGC Wildtype-specific primer without tag units: GCCACCAGC (SEQ ID NO: 39)
Anti-sense PCR primer: GCCGATCAGACGACGAC (SEQ ID NO: 40)
Sense PCR primer: GACTGAATATAAACTTGTGGTAGTTG Method:

Several cDNA synthesis reactions were carried out with the same amount of KRAS wildtype RNA standard (10^7 copies) as template. The reaction contains a mixture of two wildtype-specific primers: one primer with the 5' tail of unrelated sequence or tag units (5'-tail primer) and the other without a tail sequence (blocking primer). The ratios of the blocking primer over the 5'-tail primer vary: 0/1; 8/0; 80/1; 800/1. While the cDNA product resulted from the 5'-tail primer could be amplified, the cDNA product derived from the blocking primer will not be amplified during the PCR step due to the lack of binding site for the anti-sense PCR primer.

Figure 6:
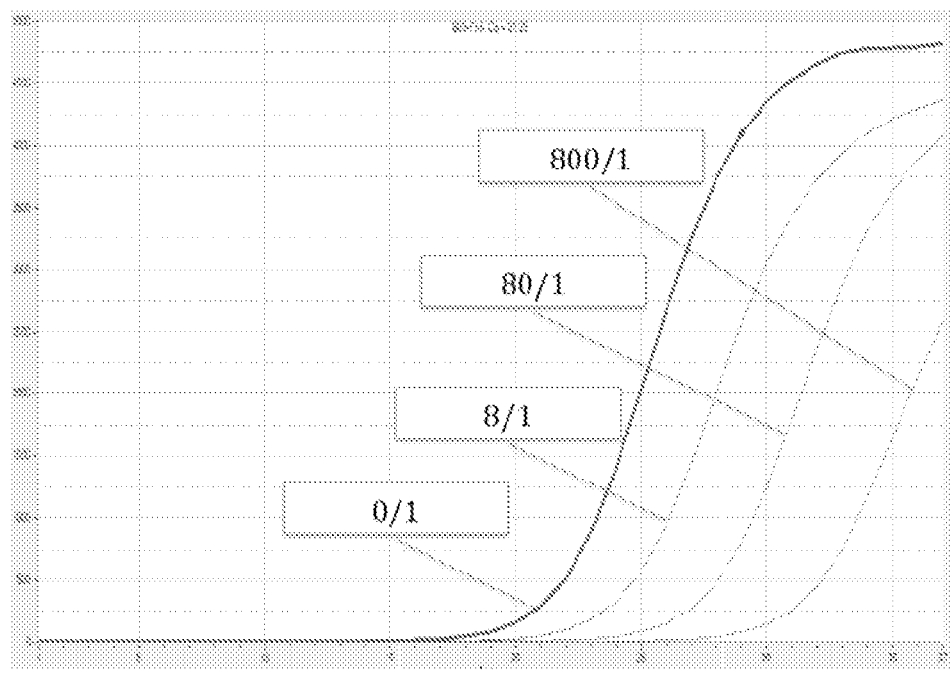
FIG. 6 depicts example of the suppression of RT-PCR product derived from certain RNA variant (for example, the abundant variant), thus theoretically enriching RT-PCR products derived from an alternative RNA variant (for example, the rare variant)

Results:

Amplification curve is delayed gradually as the molar ratio of the blocking primer over the 5'-tail primer increases (FIG. 6). This result suggests that the RT-PCR product of an abundant RNA variant can be inhibited to certain extend (depending on the molar ratio of the blocking primer over the 5'-tail primer) in ART-PCR assays, in order to favor or enrich the amplification of the cDNA product derived from the rare RNA variant.

Example 6: ART-PCR Assays for Detection of Rare Mutant Transcript Using Melting Curve Analysis This example showed that ART-PCR assays could detect rare mutant transcript with high selectivity using the melting curve analysis and the detection is linear over a broad dynamic range. (FIG. 1 E)

Material

Sequence of BRAF wildtype RNA (first variant):
(SEQ ID NO: 41)
UGAAGACCUCACAGUAAAAAUAGGUGAUUUUGGUCUAGCUACAGUGAAAU

CUCGAUGGAGUGGGUCCCAUCAGUUUGAAC

Sequence of V600E BRAF mutant RNA (second variant):
(SEQ ID NO: 42)
UGAAGACCUCACAGUAAAAAUAGGUGAUUUUGGUCUAGCUACAGAGAAAU

CUCGAUGGAGUGGGUCCCAUCAGUUUGAAC

Mutation-specific primer (second primer):
(SEQ ID NO: 43)
5'GCCGATCAGACCAGACGACTATTATTGATTCTCTGTAG 3'

Wildtype-specific primer with tail (first primer):
(SEQ ID NO: 44)
5'GCCGATCAGACGACGACCGCCGCAGATTTCACTGTAG 3'

Wildtype-specific primer without tail (third primer):
(SEQ ID NO: 45)
5'AGATTTCACTGTAG 3'

Anti-sense PCR primer:
(SEQ ID NO: 46)
5' CGATCAGACGACGAC 3'

Sense PCR primer:
(SEQ ID NO: 47)
5'AGACCTCACAGTAAAAATAGGTGA 3'

Method:

We prepared several mixtures of two BRAF RNA variants, the first variant (BRAF wildtype RNA) and the second variant (BRAF V600E mutant RNA) with different ratios. Particularly, we mixed 10^5 copies of the second variant with various copy numbers of the first variant (10^5 copies to 10^-9 copies), so that the ratios of mutant BRAF V600E RNA over wildtype BRAF RNA range from 1 down to 10^-4 (1, ⅓, 10^-1, 10^-1/3, ..., 10^-4).

The assays were performed using the ART-PCR schema depicted in FIG. 1E with end-point detection of PCR products by melting curve analysis. The cDNA synthesis reaction mixture comprises the first primer (2 nM) specific to the first variant, and containing a 5' tail of unrelated sequence; the second primer (0.5 μM) specific to the second variant, and containing a 5' tail of unrelated sequence; and further comprises the third primer (2.5 μM) also specific to the first variant, but not containing a 5' tail.

The 5' tails of both the first primer and the second primer comprises of a common sequence at the 5' end (highlighted) and a discriminating sequence (underlined) in the middle of each primer. Consequently, the cDNA products derived from these two primers will be co-amplified using the same PCR primer pair shown above, and the discriminating sequence will also be amplified. On the other hand, the cDNA product initiated by the third primer annealed to the first variant will not be amplified due to lacking the binding site for the anti-sense primer. As a result, only part of cDNA product derived from the first variant is co-amplified with cDNA product derived from the second variant, thus enriching the RT-PCR product of the second variant.

In this example, the discriminating sequence of the mutation-specific primer is designed to be AT-rich and that of the wildtype-specific primer is designed to be GC-rich. As a result, the RT-PCR products derived from mutant RNA variants will have a significantly lower melting temperature than the RT-PCR products derived from wildtype RNA variants. Accordingly, the mutant and wildtype RT-PCR products can be discriminated using melting curve analysis.

Figure 7A:
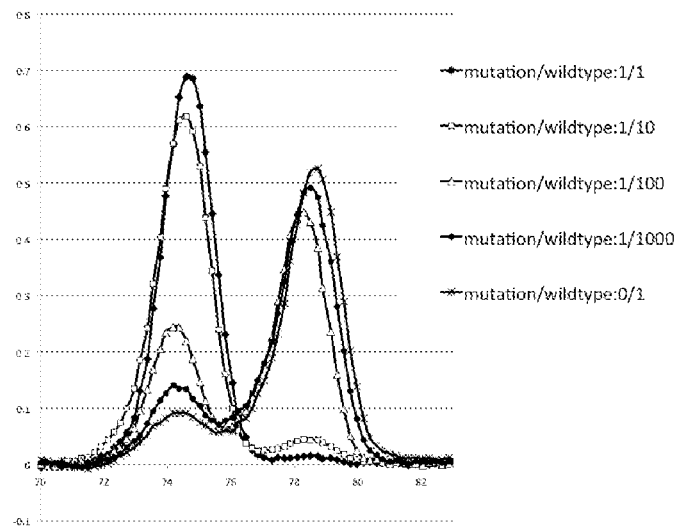
FIG. 7 depicts detection of a rare mutant RNA transcript and dynamic range of one exemplary embodiment of an ART-PCR assay using melting curve analysis.
Figure 7B:
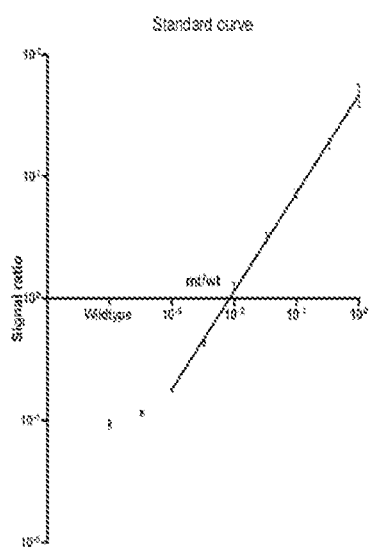

Result:

By performing the melting curve analysis in closed tube after the amplification step, we were able to simultaneously detect both the RT-PCR product derived from the second variant as a melting peak at around 75.5° C. (mutant peak) and the RT-PCR product derived from the first variant as a melting peak at around 79.6° C. (wildtype peak) (FIG. 7A). In this example, the RT-PCR product of the second variant is enriched compared to that of the first variant, so that the RT-PCR product of the second variant could be detected as a distinct peak in the RNA sample containing 1000-fold excess of the first variant. The fractions of each mutant or wildtype RT-PCR products can be calculated from the ratios of the two melting peak areas. The detection is linear over a dynamic range of more than 3 logs (FIG. 7B, $r^2$=0.9992, least-squares analysis).

Example 7: ART-PCR Assays could Also be Adapted to One-Step RT-PCR

This example showed that the cDNA synthesis reaction and polymerase chain reaction of ART-PCR assays could be performed in a single tube. (FIG. 1 F)

Materials:

```
Sequence of KRAS wildtype RNA (first variant):
                                          (SEQ ID NO: 48)
5' AUGACUGAAAAUGACUGAAUAUAAACUUGUGGUAGUUGGAGCUGGUG

GCGUAGGCAAGAGUGCCUUGACGA 3'

Sequences of KRAS mutant RNA with the mutation
sites in bold and highlighted (second variant):
                                          (SEQ ID NO: 49)
5' AUGACUGAAAAUGACUGAAUAUAAACUUGUGGUAGUUGGAGCUAGUG

GCGUAGGCAAGAGUGCCUUGACGA 3'

Wildtype-specific primer (first primer):
                                          (SEQ ID NO: 50)
5' GCCACCAGCT 3'

Mutation-specific primers (second primer):
                                          (SEQ ID NO: 51)
5' GCCGATCAGACGACGACTATTATTCCACTAGCT 3'

Sense PCR primer:
                                          (SEQ ID NO: 52)
5' TGACTGAATATAAACTTGTGGT 3'
```

Method:

Assays were performed using ART-PCR schema depicted in FIG. 1F with SYBR Green-based qPCR detection platform and reaction conditions indicated above using $10^7$ copies of either KRAS wildtype RNA (first variant) or KRAS mutant RNA (second variant) as template.

Figure 8:
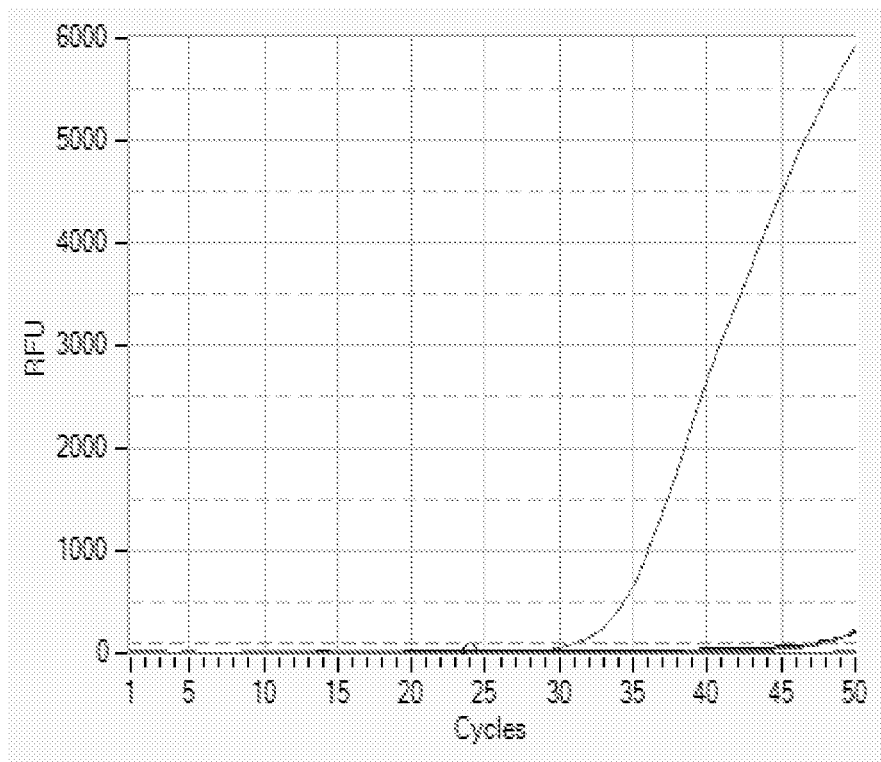
FIG. 8 depicts specificity of detection of KRAS mutant RNA transcripts using an ART-PCR assay in one exemplary embodiment with One-Step RT-PCR setting.

Result:

The specificity of ART-PCRT assay in single tube (One-Step RT-PCR) is high, as indicated by the delay in the Ct value (ΔCt) of over 16 cycles (FIG. 8). This ΔCt value corresponds to a mis-priming efficiency that accounts for about 0.0015% ($=\frac{1}{2}^{16}$) of the correct priming efficiency.

The invention claimed is:

1. Method for the detection of the presence of allele-specific RNA variants in a sample containing RNA, which is suspected to comprise one or more allele-specific RNA variants of interest, the method comprising the steps of:
   a) performing a competitive cDNA synthesis comprising a first primer specific to a first RNA variant, a second primer specific to a second RNA variant, an RNA-dependent DNA polymerase, and RNA from said sample as a template, wherein said first primer and said second primer comprise an allele-specific nucleotide portion, a target-specific sequence and tag units with a common sequence and/or a discriminating sequence so that the sequence of said tag units is not complementary to said first or second RNA variant, wherein each of the cDNA products obtained from said competitive cDNA synthesis consists of the sequence of only one primer extended by the sequence complementary to one of the target RNA variants;
   b) performing an amplification reaction so that at least part of the cDNA synthesis products obtained from step a) are amplified;
   c) detecting the presence of amplification reaction products corresponding to the first and/or second RNA variant obtained from step b) utilizing the presence of the allele-specific nucleotide portion or the discriminating sequence of said tag units in said amplification reaction products,
   wherein said first RNA variant and said second RNA variant are allelic variants of the same gene.

2. The method according to claim 1, wherein the cDNA synthesis reaction in step a) is initiated so that one or several critical components of the cDNA synthesis reaction is/are added to the reaction or activated at a temperature above the level where annealing of the first and second primers to the target sequence occurs.

3. The method according to claim 1 or 2, wherein the reaction temperature of the cDNA synthesis reaction in step a) is gradually decreased so that extension of said first primer annealed to said first RNA variant and said second primer annealed to said second RNA variant occur at an earlier timepoint than primer extension of said first primer annealed to said second RNA variant and said second primer annealed to said first RNA variant.

4. The method according to claim 1, wherein said amplification reaction of step b) is a polymerase chain reaction comprising a sense primer, an anti-sense primer and competitive cDNA products obtained from step a) as templates, wherein said sense primer comprises a 3' sequence that is complementary to the sequence present in the extended part of the competitive cDNA products, and said anti-sense primer comprises a 3' sequence that is complementary to the complement of the common sequence of said tag units.

5. The method according to claim 1, wherein said amplification reaction of step b) is a polymerase chain reaction comprising a sense primer, an anti-sense primer and competitive cDNA products obtained from step a) as templates, wherein said sense primer comprises a 3' sequence that is complementary to the sequence present in the extended part of the competitive cDNA products, and said anti-sense primer comprises a 3' sequence that is complementary to the complement of the discriminating sequence of said tag units.

6. The method according to claim 1, wherein the cDNA synthesis in step a) is a multiplex or single-plex reaction.

7. The method according to claim 1, wherein the cDNA synthesis in step a) and the amplification reaction in the step b) are performed in a single vessel.

8. The method according to claim 1, wherein said RNA is eukaryotic or bacterial mRNA, viral RNA or synthetic RNA.

9. The method according to claim 1, wherein said first and second RNA variants differ from each other by one or several nucleotide substitutions, deletions or insertions.

10. The method according to claim 1, wherein the difference between said first and second RNA variants constitutes a Single Nucleotide Polymorphism (SNP).

11. The method according to claim 1, wherein the step c) is performed by a sequence-based detector probe comprising the discriminating sequence of the first or second primer or a sequence complementary to said discriminating sequence, wherein said detector probe is present in the polymerase chain reaction of step b).

12. The method according to claim 1, wherein the step c) is performed by analyzing the melting profile of said amplification reaction products, wherein the melting profile differs between the amplification reaction products corresponding to the first and second RNA variant, and wherein this difference in the melting profile is due to the difference in the discriminating sequence of said tag units.

13. The method according to claim 1, wherein the step c) is performed by sequencing.

14. The method according to claim 1, wherein said tag units form a 5' nucleotide tail.

15. The method according to claim 1, wherein the discriminating sequence of said tag units in the first primer form a GC-rich region and the discriminating sequence of said tag units in the second primer form an AT-rich region.

16. The method according to claim 1, wherein said competitive cDNA synthesis of step a) comprises a third primer specific to the first RNA variant, wherein said third primer comprises the same or similar allele-specific nucleotide portion and target-specific sequence as the first primer but does not comprise tag units as in the first or second primers.

17. The method according to claim 16, wherein the molar amount of said third primer in said competitive cDNA synthesis is higher than the molar amount of said first or second primer or said third primer has higher affinity to the target sequence than the first primer.

18. The method according to claim 17, wherein the molar amount of said third primer in said competitive primer extension reaction is at least double compared to the molar amount of said first primer.

19. The method according to claim 16, wherein the melting temperature of the duplex of said third primer annealed to said first RNA variant is higher than the melting temperature of the duplex of said first primer annealed to said first RNA variant.

20. The method according to claim 1, wherein said first RNA variant and said second RNA variant are alternative RNA sequences at the same physical locus on a RNA segment.

21. A kit for the detection of the presence of RNA variants of human KRAS gene in a sample comprising RNA, the kit comprising a wild-type specific primer consisting of the sequence GCCACCAGCT of SEQ ID NO:16, and one primer comprising the sequence selected from the group consisting of SEQ ID NOS:17-22 specific to a second RNA variant.

22. A kit for the detection of the presence of a RNA variant of human BRAF gene in a sample comprising RNA, the kit comprising a wild-type specific primer consisting of the sequence of SEQ ID NO: 3, and one primer comprising the sequence of SEQ ID NO: 6 specific to a second RNA variant.

* * * * *

SEQUENCE LISTING

```
<160> NUMBER OF SEQ ID NOS: 52

<210> SEQ ID NO 1
<211> LENGTH: 80
<212> TYPE: RNA
<213> ORGANISM: Homo sapiens

<400> SEQUENCE: 1
ugaagaccuc acaguaaaaa uaggugauuu uggucuagcu acagugaaau cucgauggag     60 uggguccau caguuugaac                                                 80

<210> SEQ ID NO 2
<211> LENGTH: 80
<212> TYPE: RNA
<213> ORGANISM: Homo sapiens

<400> SEQUENCE: 2
ugaagaccuc acaguaaaaa uaggugauuu uggucuagcu acagagaaau cucgauggag     60 uggguccau caguuugaac                                                 80

<210> SEQ ID NO 3
<211> LENGTH: 14
<212> TYPE: DNA
<213> ORGANISM: Artificial Sequence
<220> FEATURE:
<223> OTHER INFORMATION: Synthetic primer

<400> SEQUENCE: 3
agatttcact gtag                                                      14

<210> SEQ ID NO 4
<211> LENGTH: 14
<212> TYPE: DNA
<213> ORGANISM: Artificial Sequence
```

```
<220> FEATURE:
<223> OTHER INFORMATION: Synthetic primer

<400> SEQUENCE: 4
agatttcact gtag                                                          14

<210> SEQ ID NO 5
<211> LENGTH: 14
<212> TYPE: DNA
<213> ORGANISM: Artificial Sequence
<220> FEATURE:
<223> OTHER INFORMATION: Synthetic primer

<400> SEQUENCE: 5
agatttcact gtag                                                          14

<210> SEQ ID NO 6
<211> LENGTH: 37
<212> TYPE: DNA
<213> ORGANISM: Artificial Sequence
<220> FEATURE:
<223> OTHER INFORMATION: Synthetic primer

<400> SEQUENCE: 6
gccgatcaga cgacgactat tattgatttc tctgtag                                 37

<210> SEQ ID NO 7
<211> LENGTH: 15
<212> TYPE: DNA
<213> ORGANISM: Artificial Sequence
<220> FEATURE:
<223> OTHER INFORMATION: Synthetic primer

<400> SEQUENCE: 7
cgatcagacg acgac                                                         15

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
agacctcaca gtaaaaatag gtga                                               24

<210> SEQ ID NO 9
<211> LENGTH: 71
<212> TYPE: RNA
<213> ORGANISM: Homo sapiens

<400> SEQUENCE: 9
augacugaaa augacugaau auaaacuugu gguaguugga gcuggugcg uaggcaagag         60 ugccuugacg a                                                             71

<210> SEQ ID NO 10
<211> LENGTH: 71
<212> TYPE: RNA
<213> ORGANISM: Homo sapiens

<400> SEQUENCE: 10
augacugaaa augacugaau auaaacuugu gguaguugga gcugauggcg uaggcaagag        60
ugccuugacg a                                                             71
```

```
<210> SEQ ID NO 11
<211> LENGTH: 71
<212> TYPE: RNA
<213> ORGANISM: Homo sapiens

<400> SEQUENCE: 11
augacugaaa augacugaau auaaacuugu gguaguugga gcugcuggcg uaggcaagag      60
ugccuugacg a                                                          71

<210> SEQ ID NO 12
<211> LENGTH: 71
<212> TYPE: RNA
<213> ORGANISM: Homo sapiens

<400> SEQUENCE: 12
augacugaaa augacugaau auaaacuugu gguaguugga gcuguuggcg uaggcaagag      60
ugccuugacg a                                                          71

<210> SEQ ID NO 13
<211> LENGTH: 71
<212> TYPE: RNA
<213> ORGANISM: Homo sapiens

<400> SEQUENCE: 13
augacugaaa augacugaau auaaacuugu gguaguugga gcuaguggcg uaggcaagag      60
ugccuugacg a                                                          71

<210> SEQ ID NO 14
<211> LENGTH: 71
<212> TYPE: RNA
<213> ORGANISM: Homo sapiens

<400> SEQUENCE: 14
augacugaaa augacugaau auaaacuugu gguaguugga gcucguggcg uaggcaagag      60
ugccuugacg a                                                          71

<210> SEQ ID NO 15
<211> LENGTH: 71
<212> TYPE: RNA
<213> ORGANISM: Homo sapiens

<400> SEQUENCE: 15
augacugaaa augacugaau auaaacuugu gguaguugga gcuuguggcg uaggcaagag      60
ugccuugacg a                                                          71

<210> SEQ ID NO 16
<211> LENGTH: 10
<212> TYPE: DNA
<213> ORGANISM: Artificial Sequence
<220> FEATURE:
<223> OTHER INFORMATION: Synthetic primer

<400> SEQUENCE: 16
gccaccagct                                                            10

<210> SEQ ID NO 17
<211> LENGTH: 33
<212> TYPE: DNA
<213> ORGANISM: Artificial Sequence
<220> FEATURE:
<223> OTHER INFORMATION: Synthetic primer
```

```
<400> SEQUENCE: 17
gccgatcaga cgacgactat tattccatca gct                          33

<210> SEQ ID NO 18
<211> LENGTH: 32
<212> TYPE: DNA
<213> ORGANISM: Artificial Sequence
<220> FEATURE:
<223> OTHER INFORMATION: Synthetic primer

<400> SEQUENCE: 18
gccgatcaga cgacgactat tattccagca gc                           32

<210> SEQ ID NO 19
<211> LENGTH: 33
<212> TYPE: DNA
<213> ORGANISM: Artificial Sequence
<220> FEATURE:
<223> OTHER INFORMATION: Synthetic primer

<400> SEQUENCE: 19
gccgatcaga cgacgactat tattccaaca gct                          33

<210> SEQ ID NO 20
<211> LENGTH: 33
<212> TYPE: DNA
<213> ORGANISM: Artificial Sequence
<220> FEATURE:
<223> OTHER INFORMATION: Synthetic primer

<400> SEQUENCE: 20
gccgatcaga cgacgactat tattccacta gct                          33

<210> SEQ ID NO 21
<211> LENGTH: 32
<212> TYPE: DNA
<213> ORGANISM: Artificial Sequence
<220> FEATURE:
<223> OTHER INFORMATION: Synthetic primer

<400> SEQUENCE: 21
gccgatcaga cgacgactat tattccacga gc                           32

<210> SEQ ID NO 22
<211> LENGTH: 33
<212> TYPE: DNA
<213> ORGANISM: Artificial Sequence
<220> FEATURE:
<223> OTHER INFORMATION: Synthetic primer

<400> SEQUENCE: 22
gccgatcaga cgacgactat tattccacaa gct                          33

<210> SEQ ID NO 23
<211> LENGTH: 15
<212> TYPE: DNA
<213> ORGANISM: Artificial Sequence
<220> FEATURE:
<223> OTHER INFORMATION: Synthetic primer

<400> SEQUENCE: 23
cgatcagacg acgac                                              15

<210> SEQ ID NO 24
```

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
tgactgaata taaacttgtg gt                                              22

<210> SEQ ID NO 25
<211> LENGTH: 71
<212> TYPE: RNA
<213> ORGANISM: Homo sapiens

<400> SEQUENCE: 25
augacugaaa augacugaau auaaacuugu gguaguugga gcugguggcg uaggcaagag      60
ugccuugacg a                                                          71

<210> SEQ ID NO 26
<211> LENGTH: 71
<212> TYPE: RNA
<213> ORGANISM: Homo sapiens

<400> SEQUENCE: 26
augacugaaa augacugaau auaaacuugu gguaguugga gcucguggcg uaggcaagag      60
ugccuugacg a                                                          71

<210> SEQ ID NO 27
<211> LENGTH: 10
<212> TYPE: DNA
<213> ORGANISM: Artificial Sequence
<220> FEATURE:
<223> OTHER INFORMATION: Synthetic primer

<400> SEQUENCE: 27
gccaccagct                                                            10

<210> SEQ ID NO 28
<211> LENGTH: 32
<212> TYPE: DNA
<213> ORGANISM: Artificial Sequence
<220> FEATURE:
<223> OTHER INFORMATION: Synthetic primer

<400> SEQUENCE: 28
gccgatcaga cgacgactat tattccacga gc                                   32

<210> SEQ ID NO 29
<211> LENGTH: 15
<212> TYPE: DNA
<213> ORGANISM: Artificial Sequence
<220> FEATURE:
<223> OTHER INFORMATION: Synthetic primer

<400> SEQUENCE: 29
cgatcagacg acgac                                                      15

<210> SEQ ID NO 30
<211> LENGTH: 22
<212> TYPE: DNA
<213> ORGANISM: Artificial Sequence
<220> FEATURE:
<223> OTHER INFORMATION: Synthetic primer

<400> SEQUENCE: 30
```

```
tgactgaata taaacttgtg gt                                              22

<210> SEQ ID NO 31
<211> LENGTH: 71
<212> TYPE: RNA
<213> ORGANISM: Homo sapiens

<400> SEQUENCE: 31
augacugaaa augacugaau auaaacuugu gguaguugga gcugguggcg uaggcaagag     60
ugccuugacg a                                                         71

<210> SEQ ID NO 32
<211> LENGTH: 71
<212> TYPE: RNA
<213> ORGANISM: Homo sapiens

<400> SEQUENCE: 32
augacugaaa augacugaau auaaacuugu gguaguugga gcugcuggcg uaggcaagag     60
ugccuugacg a                                                         71

<210> SEQ ID NO 33
<211> LENGTH: 32
<212> TYPE: DNA
<213> ORGANISM: Artificial Sequence
<220> FEATURE:
<223> OTHER INFORMATION: Synthetic primer

<400> SEQUENCE: 33
gccgatcaga cgacgaccac cctgccacca gc                                  32

<210> SEQ ID NO 34
<211> LENGTH: 32
<212> TYPE: DNA
<213> ORGANISM: Artificial Sequence
<220> FEATURE:
<223> OTHER INFORMATION: Synthetic primer

<400> SEQUENCE: 34
gccgatcaga cgacgactat tattccagca gc                                  32

<210> SEQ ID NO 35
<211> LENGTH: 15
<212> TYPE: DNA
<213> ORGANISM: Artificial Sequence
<220> FEATURE:
<223> OTHER INFORMATION: Synthetic primer

<400> SEQUENCE: 35
cgatcagacg acgac                                                     15

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
tgactgaata taaacttgtg gt                                              22

<210> SEQ ID NO 37
<211> LENGTH: 71
<212> TYPE: RNA
```

<213> ORGANISM: Homo sapiens

<400> SEQUENCE: 37
augacugaaa augacugaau auaaacuugu gguaguugga gcuggugcg uaggcaagag    60 ugccuugacg a    71

<210> SEQ ID NO 38
<211> LENGTH: 32
<212> TYPE: DNA
<213> ORGANISM: Artificial Sequence
<220> FEATURE:
<223> OTHER INFORMATION: Synthetic primer

<400> SEQUENCE: 38
gccgatcaga cgacgaccac cctgccacca gc    32

<210> SEQ ID NO 39
<211> LENGTH: 17
<212> TYPE: DNA
<213> ORGANISM: Artificial Sequence
<220> FEATURE:
<223> OTHER INFORMATION: Synthetic primer

<400> SEQUENCE: 39
gccgatcaga cgacgac    17

<210> SEQ ID NO 40
<211> LENGTH: 26
<212> TYPE: DNA
<213> ORGANISM: Artificial Sequence
<220> FEATURE:
<223> OTHER INFORMATION: Synthetic primer

<400> SEQUENCE: 40
gactgaatat aaacttgtgg tagttg    26

<210> SEQ ID NO 41
<211> LENGTH: 80
<212> TYPE: RNA
<213> ORGANISM: Homo sapiens

<400> SEQUENCE: 41
ugaagaccuc acaguaaaaa uaggugauuu uggucuagcu acagugaaau cucgauggag    60
ugggucccau caguuugaac    80

<210> SEQ ID NO 42
<211> LENGTH: 80
<212> TYPE: RNA
<213> ORGANISM: Homo sapiens

<400> SEQUENCE: 42
ugaagaccuc acaguaaaaa uaggugauuu uggucuagcu acagagaaau cucgauggag    60
ugggucccau caguuugaac    80

<210> SEQ ID NO 43
<211> LENGTH: 37
<212> TYPE: DNA
<213> ORGANISM: Artificial Sequence
<220> FEATURE:
<223> OTHER INFORMATION: Synthetic primer

<400> SEQUENCE: 43
gccgatcaga cgacgactat tattgatttc tctgtag    37

<210> SEQ ID NO 44
<211> LENGTH: 37
<212> TYPE: DNA
<213> ORGANISM: Artificial Sequence
<220> FEATURE:
<223> OTHER INFORMATION: Synthetic primer

<400> SEQUENCE: 44
gccgatcaga cgacgaccgc cgcagatttc actgtag        37

<210> SEQ ID NO 45
<211> LENGTH: 14
<212> TYPE: DNA
<213> ORGANISM: Artificial Sequence
<220> FEATURE:
<223> OTHER INFORMATION: Synthetic primer

<400> SEQUENCE: 45
agatttcact gtag        14

<210> SEQ ID NO 46
<211> LENGTH: 15
<212> TYPE: DNA
<213> ORGANISM: Artificial Sequence
<220> FEATURE:
<223> OTHER INFORMATION: Synthetic primer

<400> SEQUENCE: 46
cgatcagacg acgac        15

<210> SEQ ID NO 47
<211> LENGTH: 24
<212> TYPE: DNA
<213> ORGANISM: Artificial Sequence
<220> FEATURE:
<223> OTHER INFORMATION: Synthetic primer

<400> SEQUENCE: 47
agacctcaca gtaaaaatag gtga        24

<210> SEQ ID NO 48
<211> LENGTH: 71
<212> TYPE: RNA
<213> ORGANISM: Homo sapiens

<400> SEQUENCE: 48
augacugaaa augacugaau auaaacuugu gguaguugga gcugguggcg uaggcaagag        60
ugccuugacg a        71

<210> SEQ ID NO 49
<211> LENGTH: 71
<212> TYPE: RNA
<213> ORGANISM: Homo sapiens

<400> SEQUENCE: 49
augacugaaa augacugaau auaaacuugu gguaguugga gcuaguggcg uaggcaagag        60
ugccuugacg a        71

<210> SEQ ID NO 50
<211> LENGTH: 10
<212> TYPE: DNA
<213> ORGANISM: Artificial Sequence
<220> FEATURE:

```
<223> OTHER INFORMATION: Synthetic primer

<400> SEQUENCE: 50
gccaccagct                                                                  10

<210> SEQ ID NO 51
<211> LENGTH: 33
<212> TYPE: DNA
<213> ORGANISM: Artificial Sequence
<220> FEATURE:
<223> OTHER INFORMATION: Synthetic primer

<400> SEQUENCE: 51
gccgatcaga cgacgactat tattccacta gct                                        33

<210> SEQ ID NO 52
<211> LENGTH: 22
<212> TYPE: DNA
<213> ORGANISM: Artificial Sequence
<220> FEATURE:
<223> OTHER INFORMATION: Synthetic primer

<400> SEQUENCE: 52
tgactgaata taaacttgtg gt                                                    22
```